United States Patent
Pollack et al.

(10) Patent No.: US 9,878,021 B2
(45) Date of Patent: Jan. 30, 2018

(54) COMPOSITIONS AND METHODS FOR TREATMENT OF RETINAL DEGENERATIVE DISEASES

(71) Applicant: MOR RESEARCH APPLICATIONS LTD., Tel Aviv (IL)

(72) Inventors: Ayala Pollack, Tel Aviv (IL); Zeev Dvashi, Tel Aviv (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 0 days.

(21) Appl. No.: 14/894,347

(22) PCT Filed: May 29, 2014

(86) PCT No.: PCT/IL2014/050485
§ 371 (c)(1),
(2) Date: Nov. 26, 2015

(87) PCT Pub. No.: WO2014/192000
PCT Pub. Date: Dec. 4, 2014

(65) Prior Publication Data
US 2016/0114006 A1    Apr. 28, 2016

Related U.S. Application Data

(60) Provisional application No. 61/828,701, filed on May 30, 2013.

(51) Int. Cl.
A61K 31/40     (2006.01)
A61K 38/17     (2006.01)
A61K 38/45     (2006.01)

(52) U.S. Cl.
CPC ............. *A61K 38/45* (2013.01); *A61K 31/40* (2013.01); *A61K 38/1709* (2013.01); *C12Y 207/11025* (2013.01)

(58) Field of Classification Search
None
See application file for complete search history.

(56) References Cited

U.S. PATENT DOCUMENTS

2010/0226878 A1* 9/2010 Zacks .................. A01K 67/027
424/85.2

FOREIGN PATENT DOCUMENTS

WO    2010048446    4/2010
WO    2016088125    6/2016

OTHER PUBLICATIONS

Chew, B.S. et al. 2010. Transcriptional activation requires protection of the TATA-binding protein Tbp1 by the ubiquitin-specific protease Ubp3. Biochemical Journal 431: 391-399. specif. p. 391.*
Cao, G. et al. 2012.published online Sep. 9, 2011. EGCG protects against UVB-induced apoptosis via oxidative stress and the JNK1/c-Jun pathway in ARPE19 cells. Molecular Medicine Reports 5: 54-59. specif. pp. 54, 55, 56.*
Herrero-Martin, G. et al. 2009. TAK1 activates AMPK-dependent cytoprotective autophagy in TRAIL-treated epithelial cells. The EMBO Journal 28: 677-687. specif. pp. 677, 682.*
Goswami, M. et al. 2001. Regulation of MAP kinase by the BMP-4/TAK1 pathway in Xenopus ectoderm. Developmental Biology 236: 259-270. specif. p. 259.*
Ben-Porath, I. et al. 2005. The signals and pathways activating cellular senescence. International Journal of Biochemistry & Cell Biology 37: 961-976. specif. p. 970.*
Ovashi Z. & Pollack A. Protective effect of TGF-betaI in RPE cells upon oxidative stress as a model for oxidative damage during dry AMD Invest. Ophthalmol Vis. Sci. 54: E-Abstract 1805. pp. 72, 2013.
Ovashi Z. & Pollack A., TGF-betaI mediates RPE cells apoptosis through caspase-3 activation. Israeli society for vision and eye research, the 33rd annual meeting, Mar. 14-15, 2013, program & abstracts pp. 132.
Zhu D. et al., BMP4 mediates oxidative stress-induced retinal pigment epithelial cell senescence and is overexpressed in age-related macular degeneration. J Biol Chem. Apr. 3, 2009;284(14):9529-39.
Shibuya H. et al., TAB1 : an activator of the TAK1 MAPKKK in TGF-beta signal transduction. Science. May 24, 1996;272 (5265): 1179-82.

* cited by examiner

*Primary Examiner* — Renee Claytor
*Assistant Examiner* — Sharon M. Papciak
(74) *Attorney, Agent, or Firm* — JMB Davis Ben-David

(57) ABSTRACT

This disclosure relates to compositions for use in treatment of a retinal degenerative disease, such as age related macular degeneration. The described compositions include agents for activating p38 and/or JNK signaling through the activation of TAK1 in the retinal pigment epithelium of a subject diagnosed with the disease. Methods of treatment of a retinal degenerative disease using the described compositions are also provided.

5 Claims, 10 Drawing Sheets

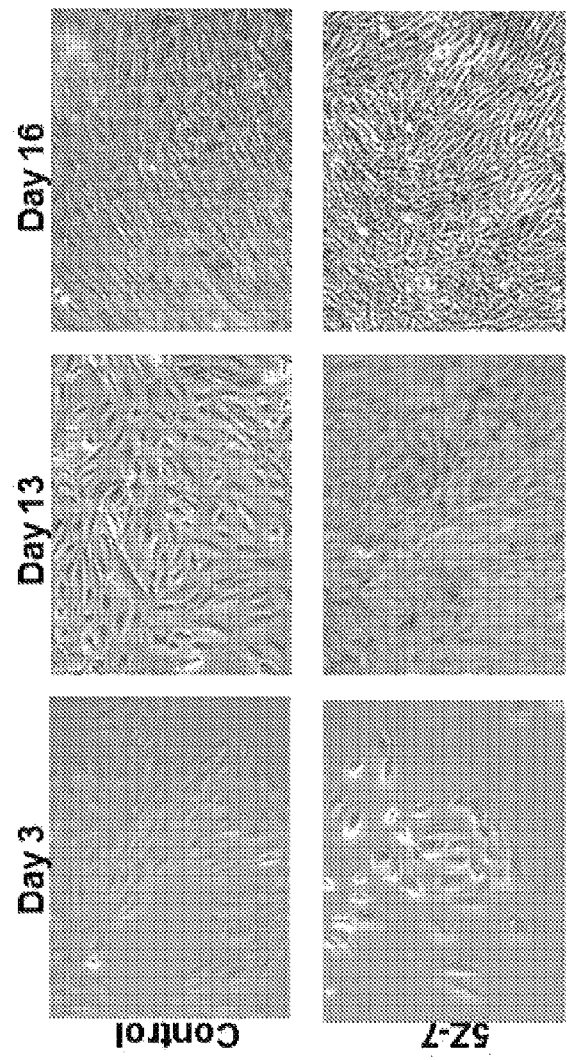
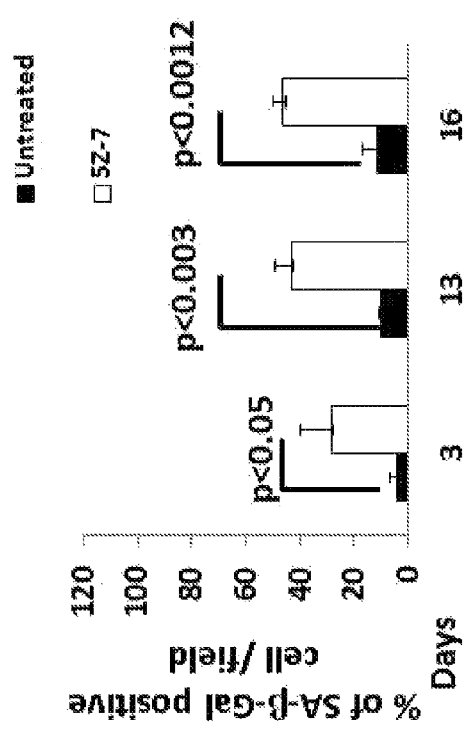
Fig. 2A
Fig. 2B

COMPOSITIONS AND METHODS FOR TREATMENT OF RETINAL DEGENERATIVE DISEASES

CROSS-REFERENCE TO RELATED APPLICATIONS

This is the U.S. National Stage of International Application No. PCT/IL2014/050485, filed May 29, 2014, which was published in English under PCT Article 21(2), and which in turn claims the benefit of U.S. Provisional Patent Application No. 61/828,701, which was filed on May 30, 2013; the contents of which are incorporated by reference herein in their entirety.

FIELD

This disclosure relates to compositions for use in treatment of a retinal degenerative disease, such as age related macular degeneration. The described compositions include agents for activating p38 and/or JNK signaling in the retinal pigment epithelium of a subject diagnosed with the disease. Methods of treatment of a retinal degenerative disease using the described compositions are also provided.

BACKGROUND

Age-related macular degeneration (AMD) remains a major cause of blindness in the industrial world (1). The frequency of AMD increases with age, affecting 2% of the population at age 50, and 25% by age 80; and affects as many as 1.5 million Americans, and millions more around the world. There are two forms of AMD: "dry" and "wet". Dry AMD affects 85-90% of people with AMD, and is a chronic, asymptomatic disease that at the early stages may cause some degree of visual impairment, and may progress to legal blindness in the advanced stage of the disease. In the early stages of dry AMD, insoluble extracellular aggregates called drusen accumulate in the retina and are associated with decreased vision (1). The late stage of dry AMD, also known as geographic atrophy (GA), is characterized by scattered or confluent areas of degeneration of retinal pigment epithelial (RPE) cells and the overlying light-sensing retinal photoreceptor cells, which rely on the RPE for trophic support.

Wet AMD affects only 10%-15% of AMD patients, emerges abruptly and rapidly progresses to blindness. The advanced stage of the wet AMD is characterized by choroidal neovascularization (CNV), wherein new choroidal blood vessels emerge from the choroid toward the outer retina. Since the main pathology of wet AMD is the formation of new blood vessels, treatment of affected patients with anti-angiogenesis drugs have been proposed to reduce the risk of blindness. Accordingly, anti-angiogenic drugs such as bevacizumab and ranibizumab are commonly prescribed to treat for wet AMD, and which have been proven to halt the deterioration of vision and benefit many wet AMD patients.

Little is known about the growth factor and microenvironment mediating pathologic changes in early and advanced forms of dry AMD. In 2001, the Age-Related Eye Disease Study showed that daily high doses of the antioxidants beta-carotene, vitamins C and E, zinc, and copper decreased the risk of progression from early to advanced AMD in patients with intermediate forms of dry AMD (2). Other treatment strategies proposed for dry AMD include modulation of the visual cycle. By disrupting the conversion of retinol to rhodopsin, the key metabolite of phototransduction, toxic waste products such as lipofuscin and A2E are decreased in the RPE (3). Proposed treatments to this end include ACU-4429 and fenretinide. Fenretinide is a synthetic retinoid derivative that competes with retinol in the circulation by binding retinol-binding protein. The ensuing complex is small enough to be excreted through the kidneys, thereby decreasing the available pool of retinol for uptake at the RPE. Additionally, International Patent Publication No. WO 2006/127945 discloses compounds and compositions that have been shown to reduce the formation of A2E. These compounds are designed to inhibit A2E biosynthesis by reducing the amount of free RAL available for reaction with PE in photoreceptor outer segments, which is the first step in the A2E biosynthetic pathway.

Other approaches for treating macular degeneration have been proposed, including use of neurotrophic receptor agonists, anti-inflammatory compounds including complement cascade inhibitors, anti-apoptosis compounds, steroids and anti-oxidant compounds (1). However, these and the other described treatments do not address the pathological cellular degeneration and senescence of the RPE cells that are most closely associated with the disease. Thus, a continuing need exists for treatments of AMD, and which potentially could be efficacious for other retinal degenerative diseases.

SUMMARY

Provided herein are pharmaceutical compositions which include a therapeutically effective amount of an agent that activates at least one of the transforming growth factor β activated kinase 1 (TAK1) and p38 or JNK signaling pathways in retinal pigment epithelial (RPE) cells in a subject, wherein the composition can be used for treating a retinal degenerative disease in the subject. Exemplary compositions include a therapeutically effective amount of anisomycin, or a functional derivative thereof.

Also provided are methods of treating a retinal degenerative disease in a subject by administering to the subject a therapeutically effective amount of an agent, such as anisomycin, TAK1 binding protein, or functional derivative thereof, that activates the at least one of the TAK1, p38 or JNK signaling pathways in retinal pigment epithelial (RPE) cells in the subject.

The foregoing and other objects, features, and advantages will become more apparent from the following detailed description, which proceeds with reference to the accompanying figures.

BRIEF DESCRIPTION OF THE DRAWINGS

FIG. 1 shows that TAK1 is involved in apoptosis and cell-cycle arrest at G0/G1 in RPE cells.

FIG. 2 shows that TAK1 inhibition increases SA-β-gal expression (senescence marker) in RPE cells subjected to oxidative stress. FIG. 2A are representative photographs showing SA-β-gal staining of RPE cells treated at the indicated times with TAK1 inhibitor 5Z-7-oxozeaenol or left untreated. FIG. 2B is a histogram representing the relative amounts of cells that were stained positively with SA-β-gal (% of cells/field) in inhibitor-treated and untreated cells on the indicated days.

FIG. 3 shows that TAK1 inhibition affects p53 expression during oxidative stress.

FIG. 6 shows that oxidative stress and TAK1 inhibition increases cell size and SA-β-gal expression in RPE cells.

FIG. 8 illustrates that treatment with anisomycin is not toxic for RPE cells in low concentration.

BRIEF DESCRIPTION OF THE DESCRIBED SEQUENCES

Figure 1A:
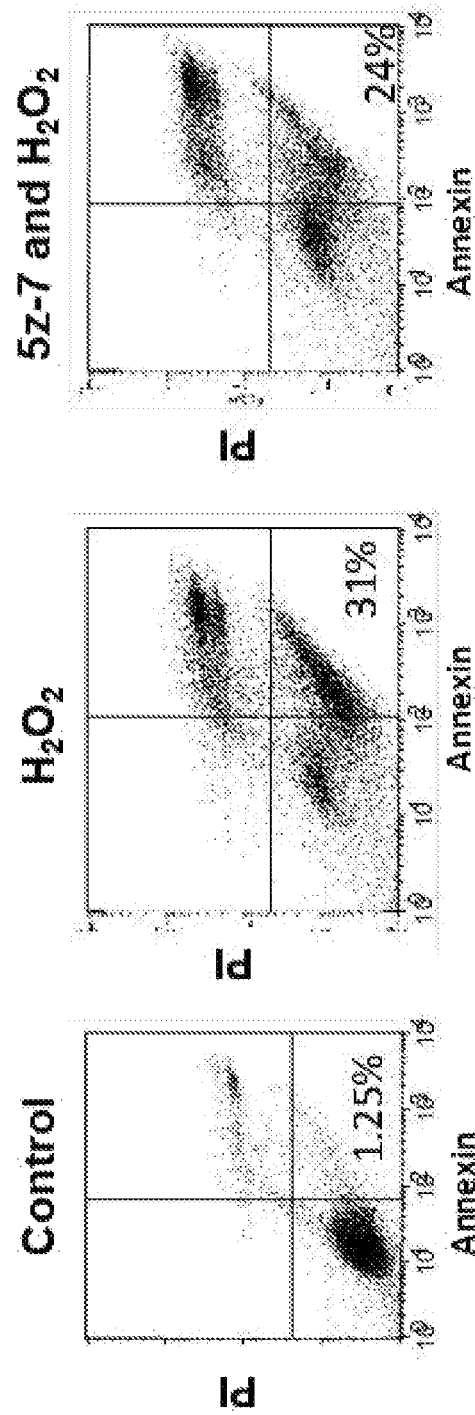
FIG. 1A are plotted results from a FACS analysis of a double-staining (annexin and propidium iodide (PI)) assay of RPE cells that were untreated (left), treated with $H_2O_2$ (center), or treated with $H_2O_2$ and the TAK1 inhibitor 5Z-7-oxozeaenol (right).

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named MORR5seqlist.txt, created May 30, 2014, about 23 KB, which is incorporated by reference herein. In the accompanying sequence listing:

SEQ ID NO. 1 is amino acid sequence of human TAK1, isoform A.

SEQ ID NO. 2 is amino acid sequence of human TAK1, isoform B.

SEQ ID NO. 3 is amino acid sequence of human TAK1, isoform C.

SEQ ID NO. 4 is amino acid sequence of human TAK1, isoform D.

SEQ ID NO. 5 is amino acid sequence of human TAK1 binding protein.

DETAILED DESCRIPTION

I. Abbreviations

AMD Age-related macular degeneration
RPE Retinal pigment epithelium
TAK1 Transforming growth factor-beta activated kinase 1

II. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Abnormal: Deviation from normal characteristics. Normal characteristics can be found in a control, a standard for a population, etc. For instance, where the abnormal condition is a disease condition, such as a retinal degenerative disease, a few appropriate sources of normal characteristics might include an individual who is not suffering from the disease (e.g., dry AMD), a population standard of individuals believed not to be suffering from the disease, etc.

Likewise, abnormal may refer to a condition that is associated with a disease. The term "associated with"

includes an increased risk of developing the disease as well as the disease itself. For instance, a certain abnormality (such as reduced central vision) can be described as being associated with the biological condition of early AMD and tendency to develop advanced AMD and complete vision loss.

Administration: The introduction of a composition, such as an agent that activates p38 and/or JNK signaling via TAK1 activation, into a subject by a chosen route. Administration of an active compound or composition can be by any route known to one of skill in the art. Administration can be local or systemic. Examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as biocompatible intraocular implants, which release the active agents and compounds over extended time intervals for sustained treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in *Remington (The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound. It is acknowledged that these terms may overlap in some circumstances. As used herein, a "functional derivative" of an agent, such as anisomycin, includes, analogs, derivatives, and mimetics of the agent.

Antibody: A polypeptide ligand comprising at least a light chain or heavy chain immunoglobulin variable region, which specifically recognizes and binds an epitope of an antigen, such as TAK1, p38 or JNK protein or a fragment thereof. Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("sav"), and disulfide stabilized Fv proteins ("dsFv"). The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997. In particular embodiments of the compositions and methods described herein, the active agent is an activating antibody that increases an activity of p38 and/or JNK signaling. Antibodies may function as mimics of a target protein activity, or as blockers of the target protein activity, with therapeutic effect derived therein.

Cellular senescence: Refers to the essentially irreversible growth arrest that occurs when cells that can propagate stop dividing, and is often referred to as just "senescence." Cellular senescence was formerly described as a process that reduces the proliferation (growth) of normal human cells in culture[4]. There are numerous senescence-inducing stimuli. It was demonstrated that the limited growth of human cells in culture is due in part to telomere erosion—the gradual loss of DNA at the ends of chromosomes (4). Furthermore, many senescent cells harbor genomic damage at non-telomeric sites, which also generate the persistence of DNA damage signaling needed for the senescence growth arrest. DNA double strand breaks are especially potent senescence inducers. The senescence growth arrest is not simply a halt in cell proliferation. Senescent cells show marked and distinct changes in their pattern of gene expression (5). Though a relatively new concept, RPE cellular senescence is considered a risk factor in the onset and progression of AMD (6).

Diagnosis: The process of identifying a disease or a predisposition to developing a disease, for example, a retinal degenerative disease, by its signs, symptoms, and results of various tests and methods. The conclusion reached through that process is also called "a diagnosis." Forms of optical testing commonly performed include but are not limited to physical examinations, visual field, imaging such as optical coherence tomography (OCT), and physiological tests such as electroretinography. The term "predisposition" refers to an effect of a factor or factors that render a subject susceptible to a condition, disease, or disorder, such as a retinal degenerative disease, such as a particular genetic mutation. In some examples, of the disclosed methods, testing is able to identify a subject predisposed to developing a condition, disease, or disorder, such as AMD.

Efficacy: Refers to the ability of agent to elicit a desired therapeutic effect. Efficacy also refers to the strength or effectiveness of a compound. As used herein, "enhancing efficacy" means to increase the therapeutic action of an agent.

Effective amount of a compound: A quantity of compound sufficient to achieve a desired effect in a subject being treated. An effective amount of a compound can be administered in a single dose, or in several doses, for example daily, during a course of treatment. However, the effective amount of the compound will be dependent on the compound applied, the subject being treated, the severity and type of the affliction, and the manner of administration of the compound.

Functional fragments and variants of a polypeptide: Included are those fragments and variants that maintain one or more functions of the parent polypeptide, including natural isoforms resultant from alternative splicing or transcription events. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential functions of a protein. Third, part of a polypeptide chain can be deleted without impairing or eliminating all of its functions. Fourth, insertions or additions can be made in the polypeptide chain for example, adding epitope tags, without impairing or eliminating its functions. Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications, as will be readily appreciated by those well skilled in the art. A variety of methods for labeling polypeptides and labels useful for such purposes are well known in the art, and include radioactive isotopes such as $^{32}P$, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, or 200 amino acid residues.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Variations in the cDNA sequence that result in amino acid changes, whether conservative or not, are usually minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90% or even 95% or 98% identical to the native amino acid sequence.

Mitogen-activated protein kinase signaling: MAPK kinase signaling is involved in cellular events such as growth, differentiation and stress responses (7). Four parallel MAPK pathways have been identified to date: ERK1/ERK2, JNK, p38 and ERK5 (8). These pathways are linear kinase cascades in that MAPKKK phosphorylates and activates MAPKK, and MAPKK phosphorylates and activates MAPK. Activation of these pathways regulates the activity of a number of substrates through phosphorylation. MAPK signaling cascades are involved in controlling cellular processes including proliferation, differentiation, apoptosis, and stress responses Pharmaceutically acceptable carriers: The pharmaceutically acceptable carriers useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional nontoxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Preventing or treating a disease: Preventing a disease refers to inhibiting the onset or the full development of a disease, for example inhibiting the development of complete vision loss in a person who has early dry AMD. Treatment refers to a therapeutic intervention that ameliorates a sign or symptom of a disease or pathological condition after it has begun to develop.

Retinal degenerative disease: A disease caused by deterioration of the retina, commonly associated with progressive vision loss, and particularly photoreceptor deterioration. Retinal degeneration can result from multiple causes. In particular embodiments, senescence, leading to atrophy of retinal pigment epithelium (RPE) cells can lead to photoreceptor loss. The RPE is the layer of cells that servers to protect and provide nutrition to photoreceptors. In particular retinal degenerative diseases such as but not limited to dry AMD, wet AMD, and retinitis pigmentosa, it is RPE dysfunction that results in progressive photoreceptor loss.

Small molecule: A molecule, typically with a molecular weight less than 1000, or in some embodiments, less than about 500 Daltons.

Subject: Living multi-cellular organisms, including vertebrate organisms, a category that includes both human and non-human mammals.

Subject susceptible to a disease or condition: A subject capable of, prone to, or predisposed to developing a disease or condition. It is understood that a subject already having or showing symptoms of a disease or condition is considered "susceptible" since they have already developed it.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces an effect.

Transforming growth factor-beta activated kinase 1 (TAK1): TAK1 is a member of the MAPKKK family, and was first reported as a regulator of MAP kinase signaling induced by TGF-β or oxidative stress (9). TAK1 is known to be activated by stress signals as well as proinflammatory cytokines, and is involved in activation of p38 and JNK signaling. TAK1 was originally known as MAP3K7.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

III. Overview of Several Embodiments

Provided herein are pharmaceutical compositions that include a therapeutically effective amount of an agent that activates at least one of the TAK1-activated, p38 or JNK signaling pathways in retinal pigment epithelial (RPE) cells in a subject. The described compositions can be used for treating a retinal degenerative disease in the subject.

In particular embodiments, the agent of the described compositions is selected from a group consisting of a peptide, antibody, and small molecule. In particular examples, the peptide is transforming growth factor-beta activated kinase 1 (TAK1) or the TAK1 binding protein (TAB1), which in particular examples can be provided to a subject by a nucleic acid vector expressing the TAK1 or TAB1 peptide.

In particular examples, the small molecule that activates TAK1, p38 and/or JNK signaling is anisomycin, or a functional variant thereof.

In particular embodiments, the pharmaceutical composition can be used in treatment of dry age-related macular degeneration (AMD), wet AMD, or retinitis pigmentosa.

In particular embodiments, the described pharmaceutical compositions can be formulated for injection into the ocular space of the subject, as an ocular ointment, or as eye drops for topical application. In other embodiments, the pharmaceutical composition is incorporated into an ocular implant which can be implanted within at least one eye of a subject.

In particular embodiments, the described pharmaceutical compositions include an additional agent for treatment of a retinal degenerative disease, including, but not limited to anti-inflammatory agents and antioxidants.

Additionally described herein are methods for treating a retinal degenerative disease in a subject by administering to the subject a therapeutically effective amount of an agent that activates the at least one of the TAK1, p38 or JNK signaling pathways in retinal pigment epithelial (RPE) cells in the subject.

In particular embodiments, the agent is selected from the group consisting of a peptide, for example TAK1 or TAB1; an antibody, such as an antibody that activates TAK1, p38 and/or JNK signaling; and a small molecule, for example anisomycin, or functional derivative thereof.

In particular embodiments, the retinal degenerative disease for treatment by the described methods is selected from the group consisting of dry age-related macular degeneration (AMD), wet AMD, and retinitis pigmentosa.

In particular embodiments of the described methods, the agent is formulated in a pharmaceutical composition administered to the subject by injected into the ocular space of the subject, formulated as an ocular ointment for topical administration, or formulated as eye drops for topical administration to the subject.

In particular embodiments, the agent is provided by an implant that is implanted within at least one eye of the subject.

In still further embodiments, the methods include administering to the subject an additional agent for treatment of a retinal degenerative disease. Such additional agents can be included in the pharmaceutical composition that includes the TAK1, p38-/and or JNK-signaling activating agents; and can also be administered separately to the subject either concurrently or at a different time period from the other active agents described herein.

IV. Stimulation of the MAP Kinase Pathway TAK1, p38 and/or JNK Signaling for Treatment or Prevention of Retinal Degeneration Described herein is the finding that inhibition of TAK1 MAP kinase, which is involved in activation of the p38 and JNK signaling pathways, promotes senescence and atrophy of retinal pigment epithelial (RPE) cells. Conversely, it has also been discovered that TAK1 stimulation, for example, by the small molecule anisomycin, inhibits RPE senescence. RPE dysfunction is a key factor of multiple retinal degenerative diseases, including age related macular degeneration (AMD) and retinitis pigmentosa (RP). RPE dysfunction is also a resulting consequence of pathologies associated with intravitreal injection and intravitreal implantation.

Accordingly, provided herein are compositions for use and methods of treatment and prevention for retinal degenerative diseases. The compositions and methods that include use of an active agent that promotes p38 and/or JNK signaling via upstream activation of TAK1 in RPE cells, such as a small molecule, peptide, or antibody.

In particular embodiments, the small molecule is anisomycin, or a functional derivative thereof.

Anisomycin ((2R,3S,4S)-4-hydroxy-2-(4-methoxybenzyl)-pyrrolidin-3-yl acetate; also known as flagecidin) is a translational inhibitor secreted by *Streptomyces* spp., and strongly activates the stress-activated mitogen-activated protein (MAP) kinases and p38/RK in mammalian cells, resulting in rapid induction of immediate early genes in the pathway. The structure of anisomycin is shown as Formula I:

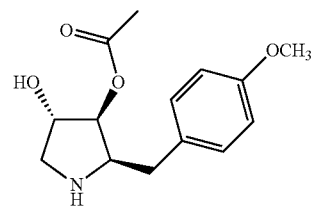 [SMILES: COc1ccc(C[C@H]2NC[C@H](O)[C@H]2OC(C)=O)cc1]

In particular embodiments, the agent for stimulation of TAK1, p38 and/or JNK signaling in RPE cells is an activating peptide of the signaling pathways. Multiple peptides are known to activate the p38 and JNK signaling pathways, including but not limited to one of the TAK1 isoforms (exemplary sequences set forth in SEQ ID NOs: 1-4), TAB1 (exemplary sequence set forth as SEQ ID NO: 5), MKK3/4/6, MLK1, ASK1, and MEKK1, which are commercially available. In particular embodiments, the peptide is formulated for direct administration to the intraocular space of a subject. In other embodiments, the active peptide is expressed from a nucleic acid vector which itself is provided to the intraocular space of the subject. Methods of recombination protein expression (including construction of a protein expressing construct based upon a peptide sequence) are commonly known in the art and are encompassed by this disclosure. It is also appreciated that functional variants of a p38 and/or JNK stimulating protein can be produced by standard methods of mutagenesis, which will maintain the activity of the wild type protein, and can be used in the compositions and methods described herein. Such functional variants can be identical in sequence to the wild type peptides by at least 98%, at least 95%, at least 90%, at least 85%, at least 80%, or even less than 80% sequence identity. It is appreciated that TAK1 was formerly called MAP3K7, and that several TAK1 isoforms exist, and this disclosure encompasses all isoforms and variants of TAK1/MAP3K7 that share p38/JNK activating catalytic activity.

In other embodiments, the p38 and/or JNK stimulating agent is an activating antibody that binds to an activating cellular receptor upstream in the p38 and/or JNK signaling pathways. In a particular example, the activating antibody specifically recognizes, binds to, and activates the TGFβ receptor 1. In other examples a TAK1-activating antibody binds to one of the multiple stress-responsive receptors upstream of TAK1 activation (eg. a member of the Toll-like Receptor (TLR) family).

The TAK1, p38 and/or JNK pathway stimulating agents described herein can be used in pharmaceutical compositions as described herein for treatment and or prevention of retinal degenerative diseases. In methods of using the described agents, a therapeutically effective amount of an agent is administered to a subject in need of such treatment. Such subjects include, patients diagnosed or predisposed to the retinal disease.

In particular examples, the subject has been diagnosed with the disease (e.g. by detection of retinal drusen; mild vision loss; loss of visual field; abnormal retinal thickness, as determined by OCT imaging; and decreased photoreceptor activity as determined by abnormal ERG results). In such examples, administration of a composition including an agent described herein can slow or halt the progression of the disease. For example, a subject diagnosed with early dry AMD who is treated could have no further degradation in visual ability and would not advance to the late stage of the disease.

In other examples, the methods described herein can be used to prevent development of a retinal degenerative disease in a subject who is predisposed to that disease. Such predisposition can be determined for example by detection of a genetic mutation associated with retinal dysfunction. Administration of an active agent described herein, and which prevents retinal degradation can thus be understood to prevent development of the disease.

Combination Therapies

In particular embodiments of the compositions and methods described herein, the agent which stimulates TAK1, p38 and/or JNK signaling is combined with at least one additional active agent to treat or prevent retinal degeneration. Non-limiting examples of active compounds for treatment or prevention of retinal degeneration include but are not limited to AMD but can be include RP, and other retinal disorders.

In some embodiments, the combination of agent which stimulates p38 and/or JNK signaling is combined and at least one additional active agent to treat or prevent retinal degeneration is administered to a subject in a single composition. In particular examples, the combination compositions are formulated so that the component active ingredients are simultaneously available in the subject in an active form. In other examples, the component active ingredients are formulated such that the components are sequentially available in an active form to the subject.

In other embodiments, the combinations of an agent which stimulates p38 and/or JNK signaling via TAK1 activation and at least one additional active agent to treat or prevent retinal degeneration can be administered to a subject in multiple compositions, one containing, for example, anisomycin, and at least one additional composition containing the at least one additional active agent. The timing and order of administration of such multiple compositions can vary. In particular examples, the compositions are provided simultaneously, but in other examples they are provided one before or after the other. It is contemplated that when administered at separate times, significant time may elapse between administration of the at least two compositions, such as several hours, several days or even longer.

Pharmaceutical Compositions and Modes of Administration

It is contemplated that the pharmaceutical agents for use in the described treatments can be supplied in any pharmaceutically acceptable compositions.

Among the pharmaceutical compositions specifically contemplated in the present disclosure are pharmaceutically acceptable acid or base addition salts of small molecules such as, but not limited to anisomycin. The phrase "pharmaceutically acceptable acid or base addition salts" includes therapeutically active non-toxic acid and non-toxic base addition salt forms which anisomycin is able to form. Such compounds which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Small molecules such as, but not limited to anisomycin which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms small molecules such as, but not limited to anisomycin, are able to form. Examples of such forms are, for instance, hydrates, alcoholates and the like.

Also contemplated for use in methods and compositions described herein are stereochemically isomeric forms of small molecules such as, but not limited to anisomycin. The term stereochemically isomeric form includes all possible compounds made up of the same atoms bonded by the same sequence of bonds, but having different three-dimensional structures that are not interchangeable. Unless otherwise mentioned or indicated, the chemical designation of a compound encompasses the mixture of all possible stereochemically isomeric forms that the compound may possess. Such mixture may contain all diastereomers and/or enantiomers of the basic molecular structure of the compound. Also contemplated are all stereochemically isomeric forms in pure form or in admixture with each other.

Various delivery systems are known and can be used to administer the peptides, antibodies, and small molecules described herein. Such systems include, for example, encapsulation in liposomes, microparticles, microcapsules, recombinant cells capable of expressing therapeutic molecule(s) (see, e.g., Wu et al., *J. Biol. Chem.* 262, 4429, 1987), construction of a therapeutic nucleic acid (expressing the described peptide or antibody) as part of a retroviral or other vector, and the like. Methods of introduction include, but are not limited to, intraocular, intrathecal, intradermal, intramuscular, intraperitoneal (ip), intravenous (iv), subcutaneous, intranasal, epidural, and oral routes. The therapeutics may be administered by any convenient route, including, for example, infusion or bolus injection, topical, absorption through epithelial or mucocutaneous linings (e.g., oral mucosa, rectal and intestinal mucosa, and the like) ophthalmic, nasal, and transdermal routes, and may be administered together with other biologically active agents.

In a specific embodiment, it may be desirable to administer the described pharmaceutical treatments by injection, catheter, suppository, or implant (e.g., implants formed from porous, non-porous, or gelatinous materials, including membranes, such as sialastic membranes or fibers), and the like. In another embodiment, therapeutic agents are delivered in a vesicle, in particular liposomes (see, e.g., Langer, *Science* 249, 1527, 1990; Treat et al., in *Liposomes in the Therapy of Infectious Disease and Cancer*, Lopez-Berestein and Fidler (eds.), Liss, N.Y., pp. 353-365, 1989).

In yet another embodiment, any one of the agents used in the combination treatments can be delivered in a controlled release system. In one embodiment, a pump may be used (see, e.g., Langer *Science* 249, 1527, 1990; Sefton *Crit. Rev. Biomed. Eng.* 14, 201, 1987; Buchwald et al., *Surgery* 88, 507, 1980; Saudek et al., *N. Engl. J. Med.* 321, 574, 1989). In another embodiment, polymeric materials can be used (see, e.g., Ranger et al., *Macromol. Sci. Rev. Macromol. Chem.* 23, 61, 1983; Levy et al., *Science* 228, 190, 1985; During et al., *Ann. Neurol.* 25, 351, 1989; Howard et al., *J. Neurosurg.* 71, 105, 1989). Other controlled release systems, such as those discussed in the review by Langer (*Science* 249, 1527 1990), can also be used.

In particular examples agents that stimulate p38 and/or JNK signaling and at least one additional agent from treatment of retinal degeneration are administered simultaneously, and by the same mode of administration. In other examples, the pharmaceutical compounds are administered at different times, and either by the same or different more of administration.

The vehicle in which the agent is delivered can include pharmaceutically acceptable compositions of the compounds, using methods well known to those with skill in the art. For instance, in some embodiments, the agents described herein are typically contained in a pharmaceutically acceptable carrier. The term "pharmaceutically acceptable" means approved by a regulatory agency of the federal or a state government or listed in the U.S. Pharmacopoeia or other generally recognized pharmacopoeia for use in animals, and, more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Water is a preferred carrier when the pharmaceutical composition is administered intravenously. Saline solutions, blood plasma medium, aqueous dextrose, and glycerol solutions can also be employed as liquid carriers, particularly for injectable solutions. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like.

Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic, if desired, can also contain minor amounts of wetting or emulsifying agents, or pH buffering agents. The therapeutics can take the form of solutions, suspensions, emulsion, tablets, pills, capsules, powders, sustained-release formulations, and the like. The therapeutic can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. A more complete explanation of parenteral pharmaceutical carriers can be found in Remington: *The Science and Practice of Pharmacy* (19th Edition, 1995) in chapter 95.

Embodiments of other pharmaceutical compositions are prepared with conventional pharmaceutically acceptable counter-ions, as would be known to those of skill in the art.

Therapeutic preparations will contain a therapeutically effective amount of at least one active ingredient, preferably in purified form, together with a suitable amount of carrier so as to provide proper administration to the patient. The formulation should suit the mode of administration.

The combination treatments of this disclosure can be formulated in accordance with routine procedures as pharmaceutical compositions adapted for intravenous administration to human beings. Typically, compositions for intravenous administration are solutions in sterile isotonic aqueous buffer. Where necessary, the compositions may also include a solubilizing agent and a local anesthetic such as lidocaine to ease pain at the site of the injection.

The ingredients in various embodiments are supplied either separately or mixed together in unit dosage form, for example, in solid, semi-solid and liquid dosage forms such as tablets, pills, powders, liquid solutions, including eye drops, ointments, or suspensions, or as a dry lyophilized powder or water free concentrate in a hermetically sealed container such as an ampoule or sachette indicating the quantity of active agent.

The amount of each therapeutic agent that will be effective will depend on the nature of the disorder or condition to be treated, as well as the stage of the disorder or condition. Effective amounts can be determined by standard clinical techniques. The precise dose to be employed in the formulation will also depend on the route of administration, and should be decided according to the judgment of the health care practitioner and each patient's circumstances. Exemplary dosages of the individual compounds are described herein, but myriad other dosage regimens are encompassed by this disclosure. An example of an additional dosage range is 0.1 to 200 mg/kg body weight in single or divided doses.

Another example of a dosage range is 1.0 to 100 mg/kg body weight in single or divided doses.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy. In a particular example, anisomycin is administered to a subject at a concentration of less then 10 ng/ml.

The therapeutic compounds and compositions of the present disclosure can be administered at about the same dose throughout a treatment period, in an escalating dose regimen, or in a loading-dose regime (e.g., in which the loading dose is about two to five times the maintenance dose). In some embodiments, the dose is varied during the course of a treatment based on the condition of the subject being treated, the severity of the disease or condition, the apparent response to the therapy, and/or other factors as judged by one of ordinary skill in the art. In some embodiments long-term treatment with the drug is contemplated.

In some embodiments, sustained localized release of the pharmaceutical preparation that comprises a therapeutically effective amount of a therapeutic compound or composition may be beneficial. Slow-release formulations are known to those of ordinary skill in the art. By way of example, polymers such as bis(p-carboxyphenoxy)propane-sebacic-acid or lecithin suspensions may be used to provide sustained localized release.

It is specifically contemplated in some embodiments that delivery is via an injected and/or implanted drug depot, for instance comprising multi-vesicular liposomes such as in DepoFoam (SkyePharma, Inc, San Diego, Calif.) (see, for instance, Chamberlain et al., *Arch. Neuro.* 50:261-264, 1993; Katri et al., *J. Pharm. Sci.* 87:1341-1346, 1998; Ye et al., *J. Control Release* 64:155-166, 2000; and Howell, *Cancer J.* 7:219-227, 2001).

The following examples are provided to illustrate certain particular features and/or embodiments. These examples should not be construed to limit the disclosure to the particular features or embodiments described.

EXAMPLES

Example 1: TAK1 Inhibition Increases Senescence of Retinal Pigment Epithelial Cells This example shows that inhibition of the TAK1 MAP kinase promotes senescence of retinal pigment epithelial (RPE) cells.

Methods

Double-staining (annexin and propidium iodide (PI)) assay of RPE cells. RPE cells (ARPE-19, available from ATCC) were treated for one hour with the TAK1 inhibitor {5Z-7-oxozeaenol (1 µM)}, following 200 µM $H_2O_2$ for one hour or left untreated. The cells were then washed with fresh medium and after 24 hours were trypsinized, stained, and analyzed by FACS. The percentage of cells in each cell-cycle phase (G1/G0, S, and G2/M) was determined by its DNA content (FL2A).

Cell viability assays ARPE-19 cells were seeded in 96-well plates (5000 cells/well) in full medium and were pretreated with the TAK1 inhibitor 5Z-7-oxozeaenol (1 µM) or left untreated for 1 hour. Their viability was then assayed by the XTT assay (cell proliferation kit cat #20-300-1000; Beit Haemek, Israel).

SA-β-gal staining was carried out as described (10).

Western blot analysis was performed by standard protocols (11), p53, p38, phospho-p38, GADPH, and TAK1; antibodies were obtained from Enco, Israel.

Results

The role of TAK1 in the inflammatory response is characterized (12, 13), but little is known about its participation in the response of RPE cells to stress. RPE cells were treated with the TAK1 inhibitor 5Z-7-oxozeaenol (1 µM) for 1 hour before further treatment with $H_2O_2$ (200 µM). Staining with annexin and propidium iodide and FACS analysis showed that compared to untreated RPE cells, in which the number of apoptotic cells expressed as a percentage of the total number was 1.25%, the number of apoptotic cells after treatment with $H_2O_2$ alone increased over the same time period to 31%. In contrast, in cells treated with the TAK1 inhibitor prior to their treatment with $H_2O_2$ the number apoptotic cells was 24% (FIG. 1A). The number of cells in the late apoptosis section of each FACS chart (annexin and Pi, upper right panel) was similar with or without TAK1 inhibitor. These results imply that TAK1 is involved in apoptosis and that its inhibition reduces this process.

Figure 1D:
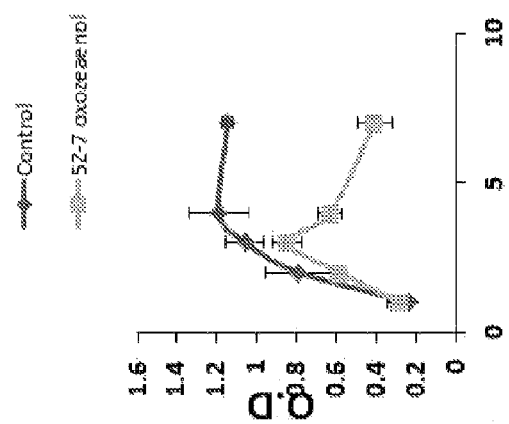
FIG. 1D is a chart illustrating the results of a XTT assay comparing viability of ARPE-19 cells pretreated with the TAK1 inhibitor 5Z-7-oxozeaenol (1 μM) or left untreated for 1 hour.
Figure 1C:
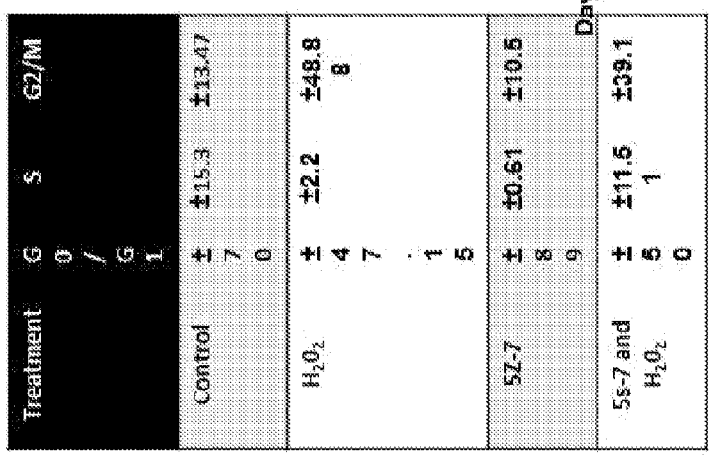
FIG. 1C presents the results of the FACS analysis of FIG. 1B in table form.
Figure 1B:
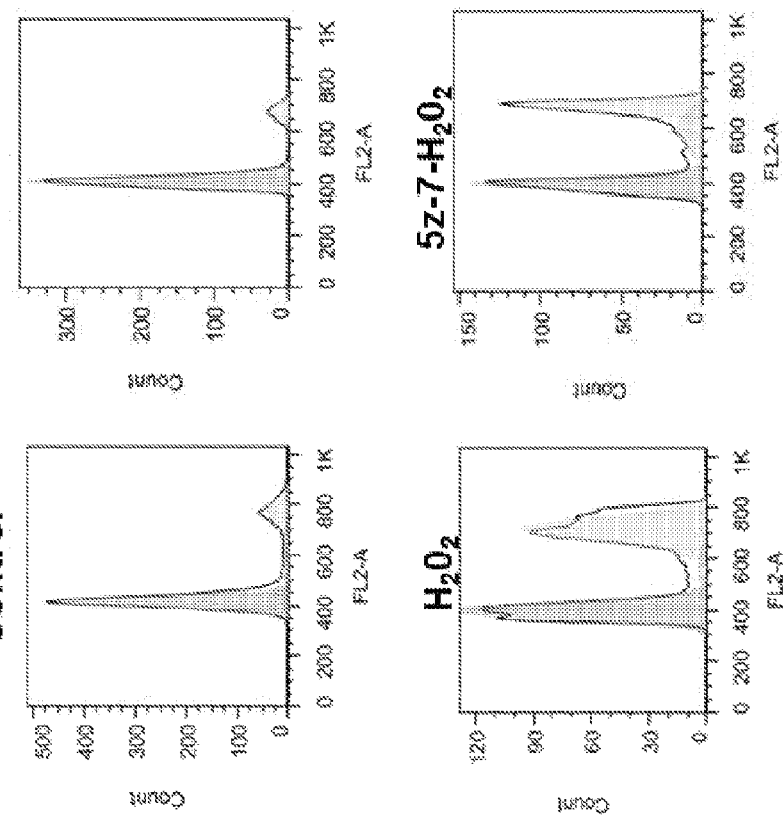
FIG. 1B shows FACS analysis and of RPE cells pretreated with the TAK1 inhibitor with or without $H_2O_2$ as described in A. The percentage of cells in each cell-cycle phase (G1/G0, S, and G2/M) was determined by its DNA content (FL2A), as reflected on the x-axis.

To examine the effect of TAK1 inhibition on the RPE cell cycle, RPE cells were treated with TAK1 inhibitor, with or without $H_2O_2$. The RPE cells are quiescent and mostly located at the G0/G1 stage (FIGS. 1B and 1C), however, following TAK1 inhibition the percentage of cells at the G0/G1 stage increased to 89% of the total number. When the cells were subjected to oxidative stress ($H_2O_2$ treatment) they exhibit high levels of G2/M arrest. This phenomenon was reduced upon TAK1 inhibition prior to the oxidative stress (FIGS. 1B and C). The Cell cycle arrest at G0/G1 upon TAK1-inhibition was further supported by the reduction in proliferation of RPE cells observed in the presence of the TAK1 inhibitor (FIG. 1D). Untreated cells showed a high rate of proliferation as reflected by their increasing optical density (O.D.), which reached a peak on day 4 in contrast to TAK1 inhibited cells which demonstrated a slower proliferation rate that began to decrease after 3 days (FIG. 1D). These findings suggested that inhibition of TAK1 promotes cell cycle arrest and RPE-cell senescence.

Figure 2C:
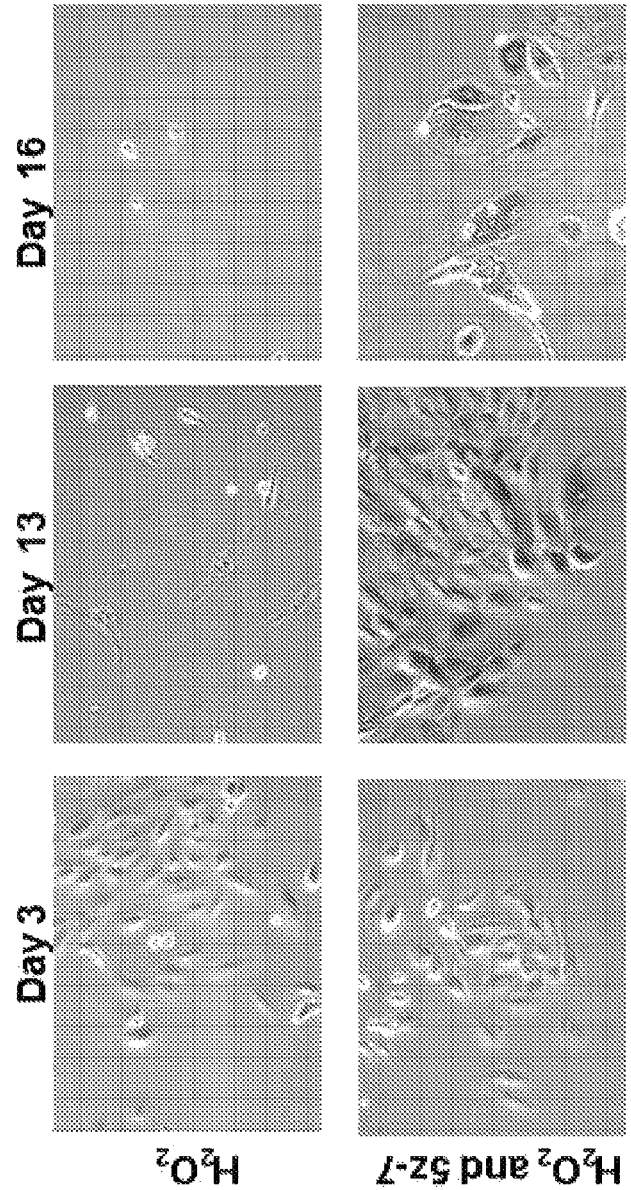
FIG. 2C are representative photographs showing SA-β-gal staining in RPE cells treated with TAK1 inhibitor for one hour and then treated with 200 μM $H_2O_2$ for 1 hour, or only with $H_2O_2$.
Figure 2D:
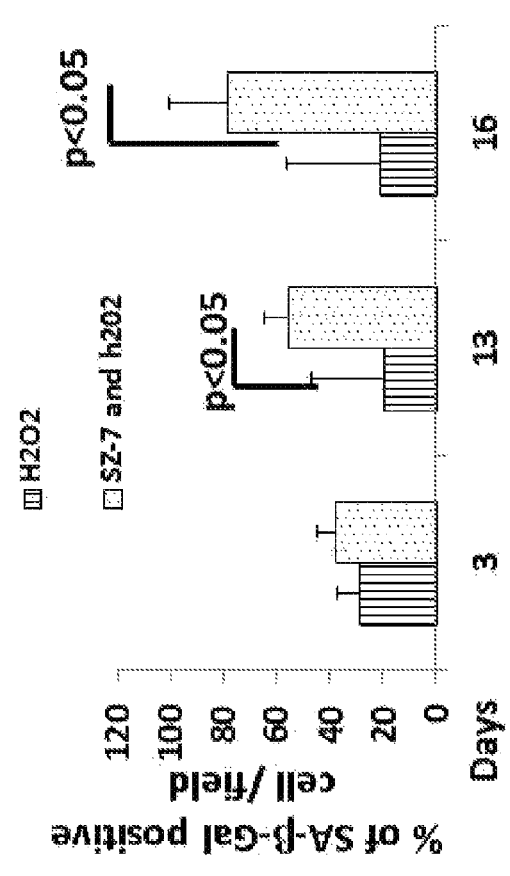
FIG. 2D is a histogram showing relative amounts of cells that were stained positively with SA-β-gal (% of cells/field) with $H_2O_2$ alone or with $H_2O_2$ combined with TAK1 inhibitor.

To further characterize the effect of TAK1 inhibition on the senescence of RPE cells, the effect of such inhibition on SA (senescence associated)-β-gal expression was examined in these cells (10). The number of cells expressing SA-β-gal dramatically increased after treatment with the TAK1 inhibitor relative to the number in untreated cells (FIGS. 2A and 2B). This increase was further enhanced when TAK1 was inhibited and the RPE cells were additionally exposed to oxidative stress (FIGS. 2C and 2D). In cells that were exposed to oxidative stress without such pretreatment there was extensive cell death, and by day 16 there were only a few surviving cells, with very low expression of SA-β-gal. In contrast, on days 13 and 16 SA-β-gal was strongly increased in cells that had been exposed to oxidative stress, after pretreatment with the TAK1 inhibitor (FIGS. 2C and D). These findings further support the participation of TAK1 in the regulation of senescence in RPE cells.

Figure 3A:
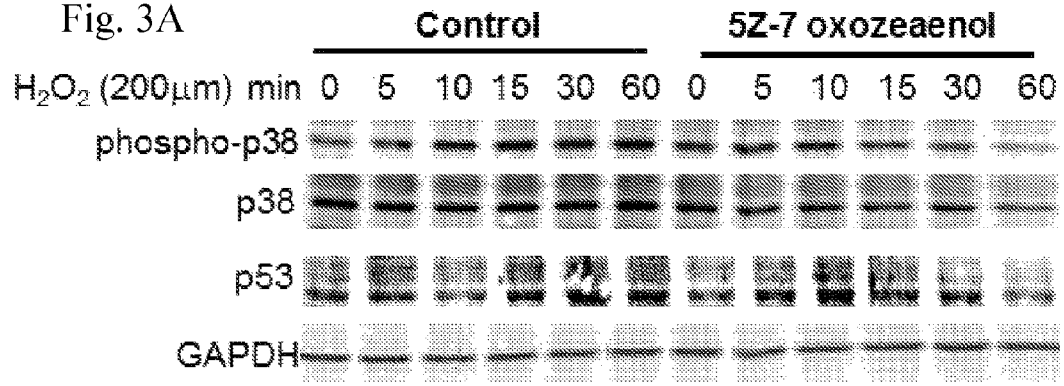
FIG. 3A shows Western blot analysis of RPE cells were treated with the TAK1 inhibitor 5Z-7-oxozeaenol (1 μM) or were left untreated for 1 hour. Separated total protein extracts were analyzed with the indicated antibodies, and normalized to GAPDH.
Figure 3B:
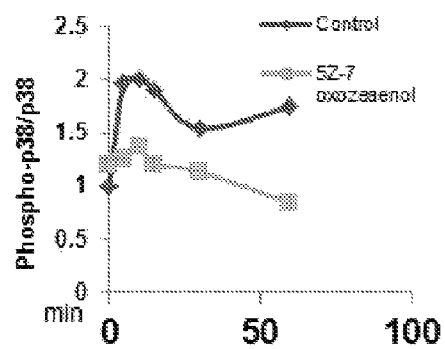
FIG. 3B is a graph presenting phospho-p38 levels normalized to p38.
Figure 3C:
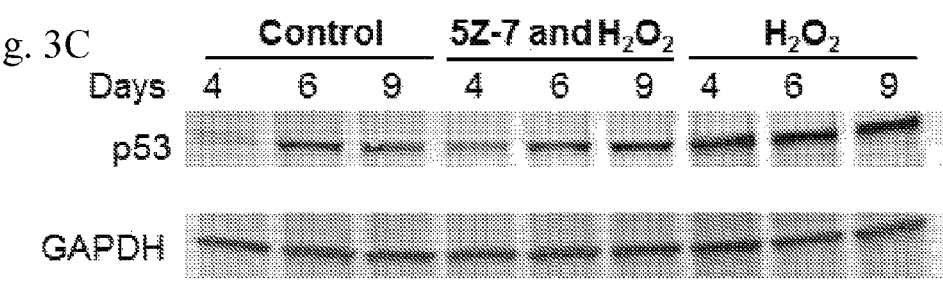
FIG. 3C shows a Western blot analysis of RPE cells left untreated, treated with $H_2O_2$, or were treated with the TAK1 inhibitor 5Z-7-oxozeaenol (1 μM), and then treated with $H_2O_2$, and grown to the indicated days.
Figure 3D:
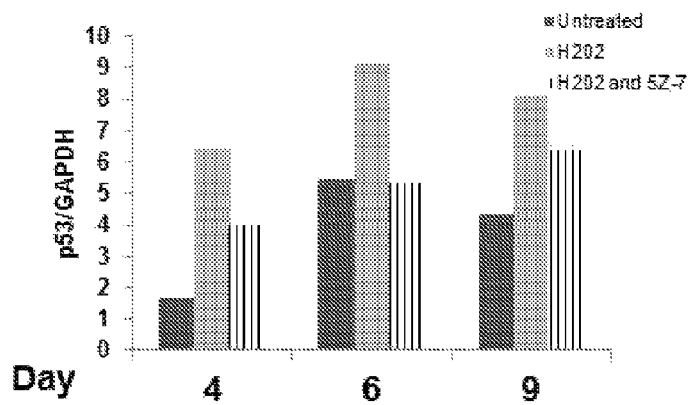
FIG. 3D is a histogram presenting the results of the Western blot of FIG. 3C. p53 levels were normalized to GAPDH (results are the mean of two independent experiments).

The p53 protein is known to play a critical role in cell-cycle regulation, DNA repair, and programmed cell death (14, 15). In view of this knowledge, and given the above-described observation that TAK1 inhibition reduced apoptosis, the expression of p53 in RPE cells was examined. As shown in FIG. 3A, p53 expression in RPE cells under oxidative stress was strongly affected by pretreatment of the cells with the TAK1 inhibitor, seen by the inhibition of p38 phosphorylation (FIGS. 3A and 3B). In control cells (without such pretreatment) the expression of p53 gradually increased, reaching a peak after 60 min, whereas in the pretreated cells p53 expression peaked after 10 min and then declined (FIG. 3A). Over a longer period, TAK1 inhibition reduced p53 expression levels slightly more than the untreated cells (FIGS. 3C and 3D). In contrast, RPE cells that were exposed to oxidative stress displayed high levels of p53 after 4 days, and its expression gradually increased (FIGS. 3C and 3D).

Figure 4:
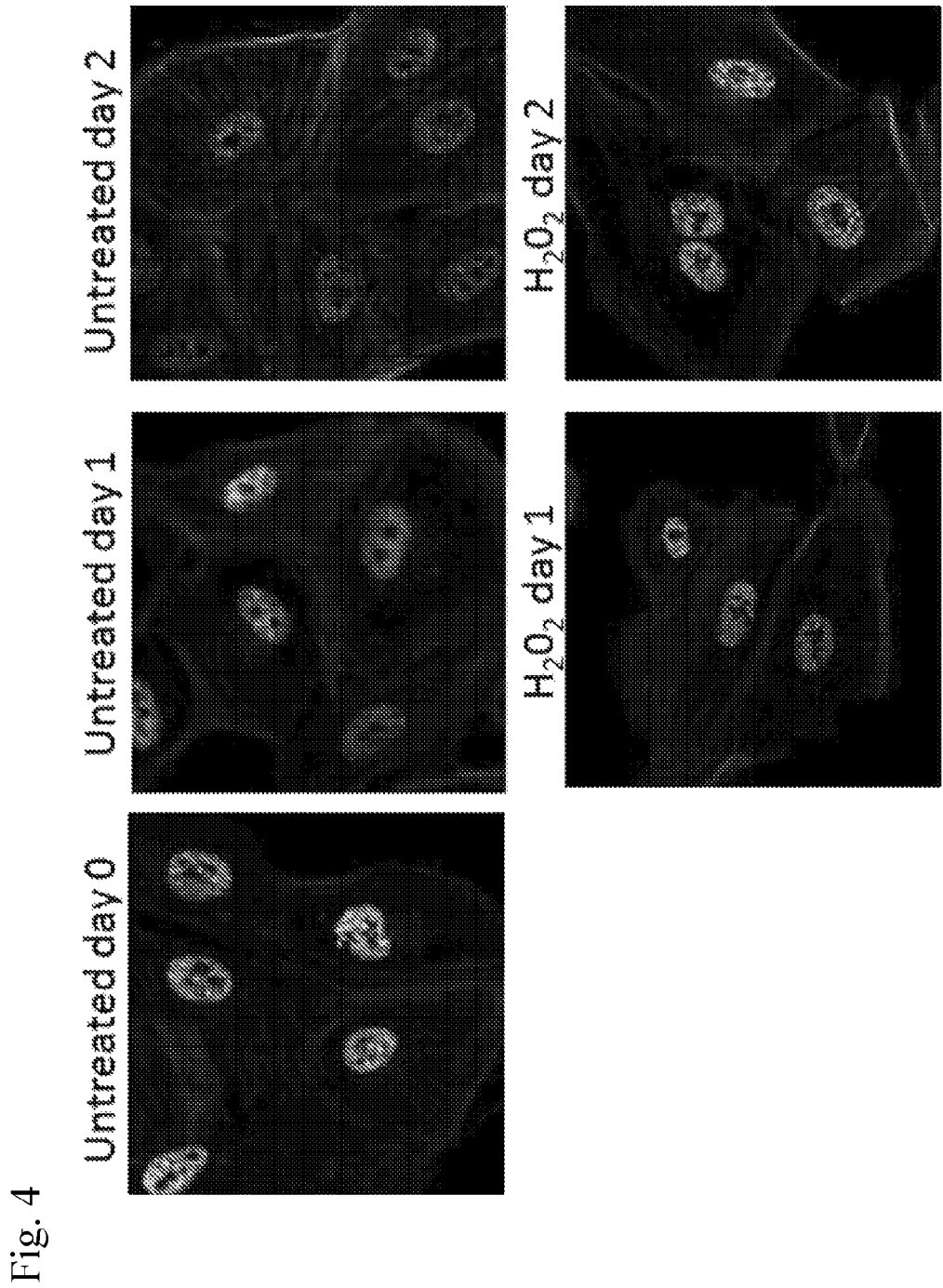
FIG. 4 shows regulation of TAK1 upon oxidative stress. Shown are representative photographs of three independent experiments in which RPE cells were treated with $H_2O_2$ (200 μM, 1 hour) or left untreated. The cells were then immunostained with TAK1 antibodies (green), actin (red) and DAPI (blue).

The extent and expression pattern of TAK1 in the RPE cells were assessed by immunofluorescence. As shown in FIG. 4, TAK1 levels in untreated cells were stable, mainly localized in the nucleus, and with no significant changes observed during the experiments. Interestingly, when the cells were exposed to oxidative stress, TAK1 expression in the nucleus decreased, and returned to normal levels only after 48 hours. This finding implies that TAK1 expression was regulated during oxidative stress, thus demonstrating its importance in this process.

Figure 5:
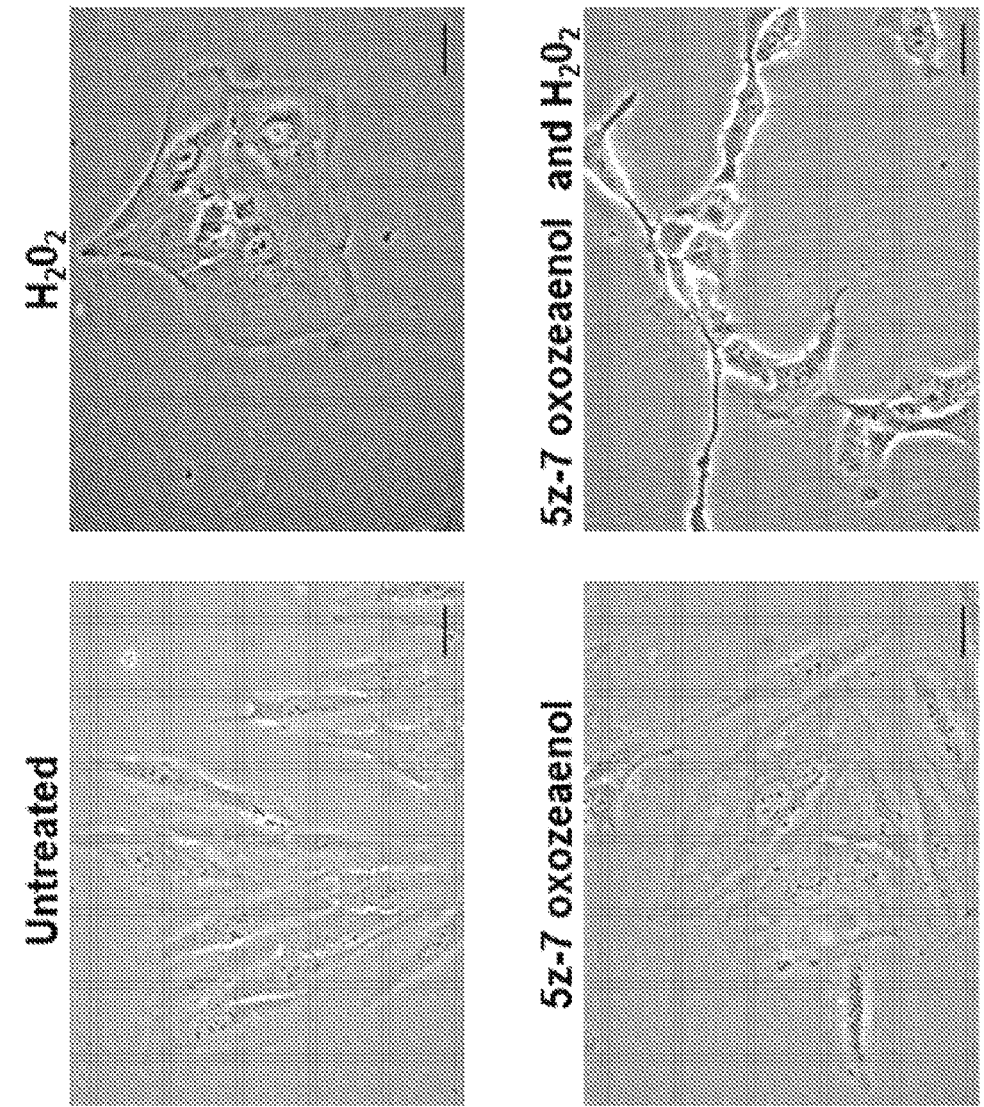
FIG. 5 presents photographs showing that TAK1 inhibition contributes to the SASP of the RPE cells, causing hypertrophy and dysfunction. RPE cells were grown with the TAK1 inhibitor and/or $H_2O_2$ (200 mM) or without treatment. After 2 weeks, conditioned media from the differently treated cells were centrifuge and the supernatants was employed on new freshly cells. Representative photographs of fresh RPE cells treated for 72 hours with the indicated conditioned media are shown. Scale bar=50 μm.

The most significant effect of senescence, is the acquisition of a senescence-associated secretory phenotype (SASP). SASP can convert senescent cells to proinflammatory cells that promote the secretion of chemokines and cytokines that can affect the microenvironment, including in the human retina (16, 17). To examine the role of TAK1 in this process, RPE cells were treated with TAK1 inhibitor or with $H_2O_2$, alone or in combination. After 2 weeks, the media was collected from the three separate treatments, centrifuged and the supernatants (conditioned media) were applied on fresh RPE cells for 72 hours. As shown in FIG. 5, the cells that received conditioned medium from untreated cells displayed a normal phenotype, whereas the cells that received conditioned medium collected from RPE cells treated with either the TAK1 inhibitor or with $H_2O_2$ demonstrated a hypertrophic phenotype similar to that of senescent cells. Interestingly, the cells that received conditioned medium from cells treated with both the TAK1 inhibitor and $H_2O_2$ demonstrated aberrant morphology similar to that of atrophic RPE cells.

Figure 6A:
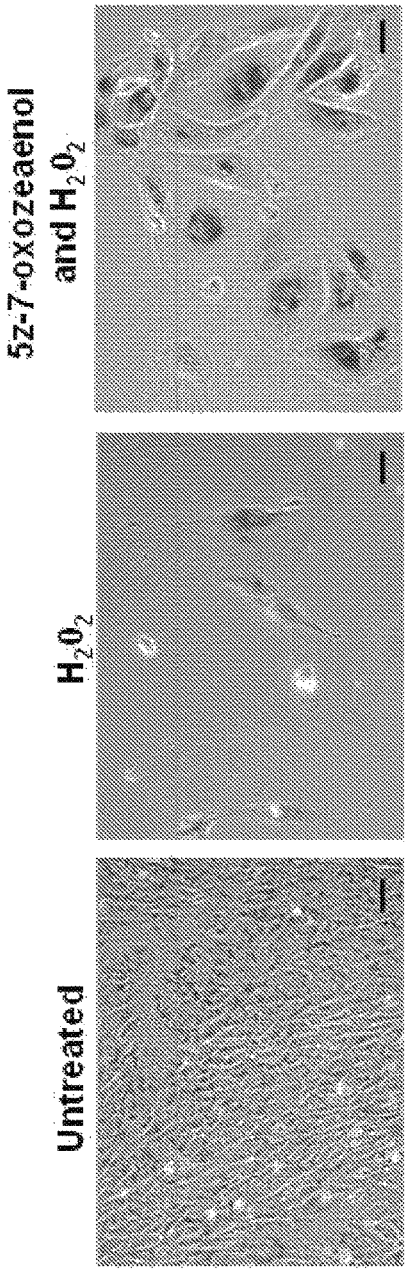
FIG. 6A shows representative photographs of the following conditions (left to right): Untreated RPE cells, mostly negatively for SA-β-gal staining, with normal morphology; RPE cells treated with oxidative stress with or without TAK-1 inhibition (5z-7 oxozeanol), RPE cells positively stained with SA-β-gal with hypertrophy, flattened and abnormal shape of the RPE cells.
Figure 6B:
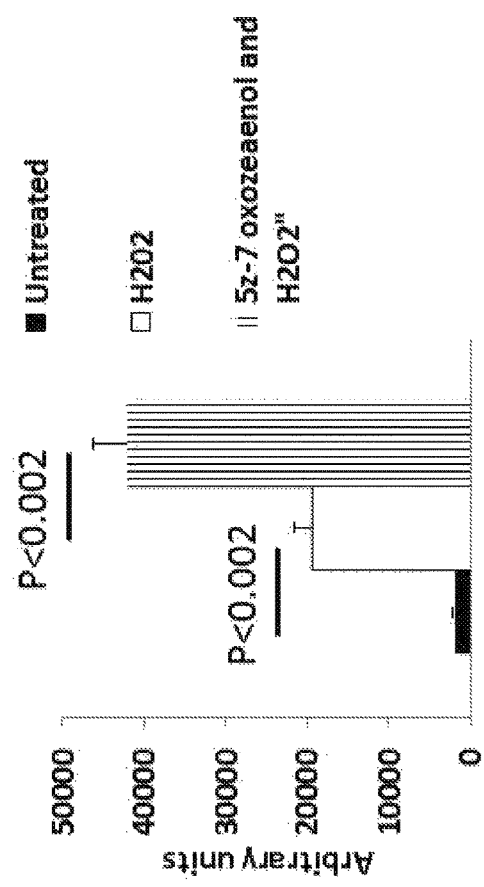
FIG. 6B shows quantification of the different cells size using Image software. N=40 cells for each treatment.

One of the hallmarks of RPE senescence is cellular hypertrophy. RPE cell size is approximately 9-12 µM; but upon oxidative stress or genetic mutation RPE cells can undergo enlargement. As shown in FIG. 6, upon stress, the cells size increase by 4-fold compared to normal cells. However, the combination of TAK1 inhibition with oxidative stress further increases cell size compared to stressed cells (without TAK1 inhibition) and normal cells.

Taken together, these results demonstrate that that TAK1 inhibition promotes RPE cellular senescence, and suggest that agents that promote the TAK1-mediated MAP kinase signaling pathway can be used to inhibit such senescence and by extension, treat RPE-senescence-associated diseases.

Example 2: Treatment with Anisomycin Reduces the Appearance of Senescence in RPE Cells The results presented in Example 1 demonstrate that inhibition of TAK1 signaling promotes RPE cellular senescence. This example shows that anisomycin, a TAK1-signalling promoting agent produces the opposite effect, and reduces RPE cellular senescence.

Methods

All methods are as previously described. Anisomycin was obtained from Sigma Aldrich, Israel.

Results

Figure 7:
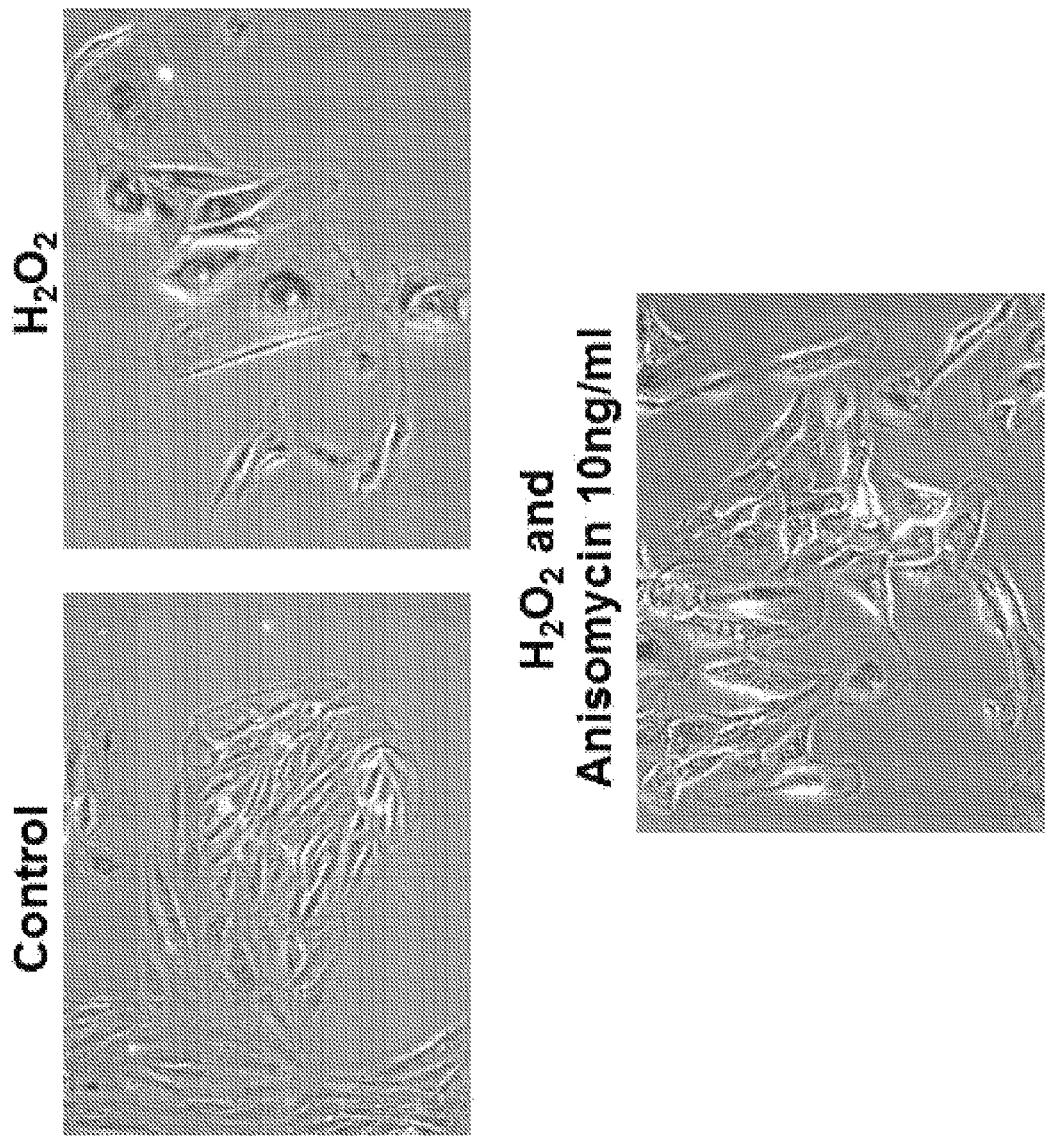
FIG. 7 shows that treatment with anisomycin reduces the appearance of (senescence marker) in RPE cells. REP cells were treated with 200 mM $H_2O_2$ for one hour or left untreated for 10 day. Following treatment (oxidative stress) the cells were treated with or without anisomycin 10 ng/ml for 5 min. Cells were then washed and grown for more than five days. Representative photographs show SA-β-gal staining of control RPE cells, or treated with oxidative stress with or without anisomycin.

Anisomycin was shown to activate kinases associated to the to the MAP kinase such as TAK1. To determine the effects of anisomycin treatment on RPE cells, RPE cells were treated with $H_2O_2$ for 1 hour. Following this treatment, the cells were grown in fresh medium for additional 10 days until appearance of senescence markers. After the tenth day, the cells were treated with anisomycin and grown in fresh medium for an additional five days, stained for the presence of SA-β-Gal, and photographed. Illustrative photographs are shown in FIG. 7. As can be seen in the figure, treatment with anisomycin reduces the number of SA-β-Gal positive cells in comparison to untreated cells exposed to oxidative stress.

Figure 8A:
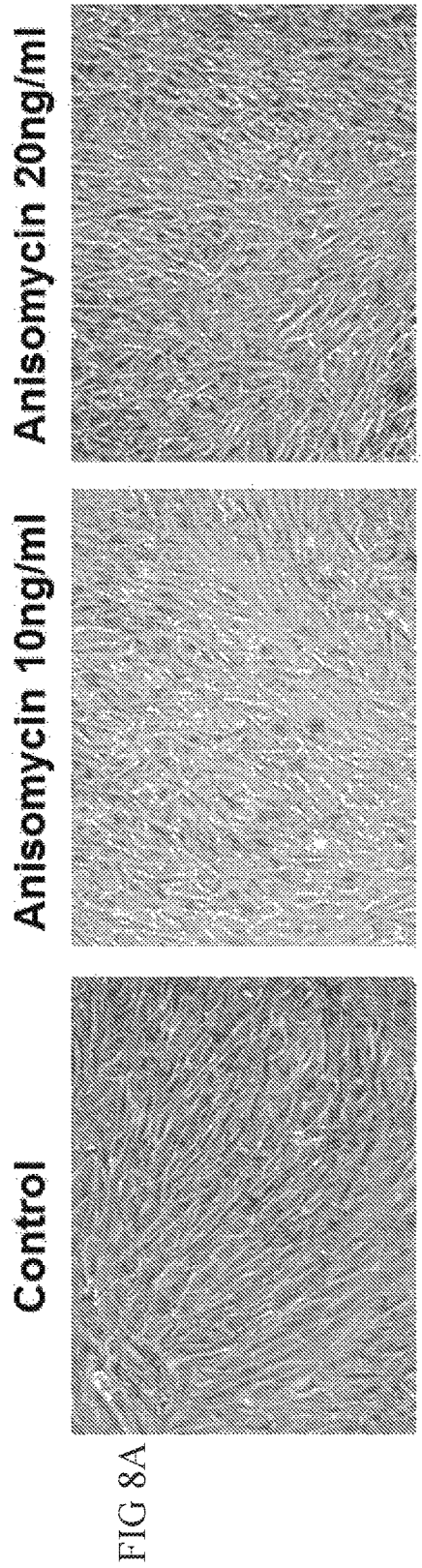
FIG. 8A shows representative photographs showing SA-β-gal staining of RPE cells treated with different anisomycin concentrations or left untreated, as indicated.
Figure 8B:
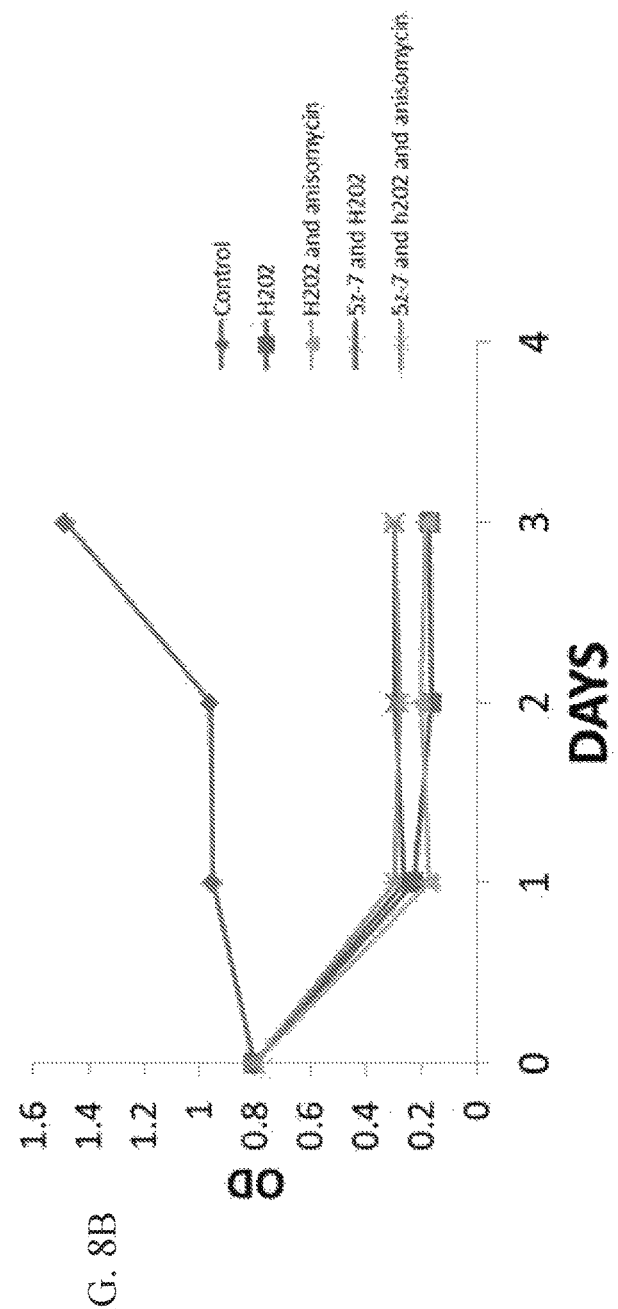
FIG. 8B: ARPE-19 cells were seeded in 96-well plates (5000 cells/well) in full medium and were pretreated with the TAK1 inhibitor 5Z-7-oxozeaenol (1 μM), $H_2O_2$, and Anisomycin alone or in combination or left untreated for 1 hour. Their viability was then assayed by the XTT assay. The experiment was performed in triplicate.

To determine possible toxicity of anisomycin to RPE cells, RPE cells were treated with anisomycin at different concentration for 5 minute periods. Following treatment, the medium was replaced and fresh medium was added. 72 hours post-treatment, the cells were photographed. As can be seen in FIG. 8A cellular morphology was similar to the control cells, thus demonstrating that in low levels anisomycin is not toxic. Furthermore, the rate of cell proliferation with oxidative stress and anisomycin did not display reduction in the rate of cells proliferation. FIG. 8B shows ARPE-19 cells that were pretreated with the TAK1 inhibitor 5Z-7-oxozeaenol (1 µM), $H_2O_2$, and anisomycin alone or in combination, or left untreated for 1 hour. Their viability was then assayed by the XTT assay.

Together these results indicate that anisomycin can inhibit cellular senescence in RPE cells subject to oxidative stress.

Example 3: Treatment of AMD with Aniosomycin

This example describes the treatment of early stage dry AMD with a pharmaceutical composition that includes anisomycin.

Subjects are identified that have been diagnosed with dry AMD. Diagnostic criteria include one or more of detection of retinal drusen; mild vision loss; loss of visual field; abnormal retinal thickness, as determined by OCT imaging; and decreased photoreceptor activity as determined by abnormal ERG results.

Subjects are provided anisomycin formulated as eye drops, and instructed to apply one drop in each eye, once a day. In an additional trial, subjects are administered anisomycin by intraocular injection once a week. Every two month for the first six months of treatment, subjects are examined for disease progression. Afterwards, subjects are examined every six months. If no change in disease state is detected, subjects are instructed to maintain treatment. If increased drusen or other signs of disease progression are detected, subjects are instructed to increase the anisomycin dosage to two or three drops in each eye every day, or are administered additional injections or injections of greater anisomycin dosage.

REFERENCES

1. Ambati J, Fowler B J: Mechanisms of age-related macular degeneration, Neuron 2012, 75:26-39
2. A randomized, placebo-controlled, clinical trial of high-dose supplementation with vitamins C and E, beta carotene, and zinc for age-related macular degeneration and vision loss: AREDS report no. 8, Archives of ophthalmology 2001, 119:1417-1436
3. Iriyama A, Fujiki R, Inoue Y, Takahashi H, Tamaki Y, Takezawa S, Takeyama K, Jang W D, Kato S, Yanagi Y: A2E, a pigment of the lipofuscin of retinal pigment epithelial cells, is an endogenous ligand for retinoic acid receptor, J Biol Chem 2008, 283:11947-11953 4. Rodier F, Campisi J: Four faces of cellular senescence, J Cell Biol 2011, 192:547-556
5. Saretzki G, Feng J, von Zglinicki T, Villeponteau B: Similar gene expression pattern in senescent and hyperoxic-treated fibroblasts, J Gerontol A Biol Sci Med Sci 1998, 53:B438-442
6. Kozlowski M R: RPE cell senescence: a key contributor to age-related macular degeneration, Medical hypotheses 2012, 78:505-510
7. Nishida E, Gotoh Y: The MAP kinase cascade is essential for diverse signal transduction pathways, Trends in biochemical sciences 1993, 18:128-131
8. Gotoh Y, Nishida E: [MAP kinase kinase/MAP kinase cascade], Tanpakushitsu kakusan koso Protein, nucleic acid, enzyme 1993, 38:1625-1628
9. Huangfu W C, Omori E, Akira S, Matsumoto K, Ninomiya-Tsuji J: Osmotic stress activates the TAK1-JNK pathway while blocking TAK1-mediated NF-kappaB activation: TAO2 regulates TAK1 pathways, J Biol Chem 2006, 281:28802-28810
10. Dimri G P, Lee X, Basile G, Acosta M, Scott G, Roskelley C, Medrano E E, Linskens M, Rubelj I, Pereira-Smith O, et al.: A biomarker that identifies senescent human cells in culture and in aging skin in vivo, Proc Natl Acad Sci USA 1995, 92:9363-9367
11. Chuderland D, Dvashi Z, Kaplan-Kraicer R, Ben-Meir D, Shalgi R, Lavi S: De novo synthesis of protein phosphatase 1A, magnesium dependent, alpha isoform (PPM1A) during oocyte maturation, Cell Mol Biol Lett 2012, 17:433-445
12. Kim S I, Kwak J H, Zachariah M, He Y, Wang L, Choi M E: TGF-beta-activated kinase 1 and TAK1-binding protein 1 cooperate to mediate TGF-beta1-induced MKK3-p38 MAPK activation and stimulation of type I collagen, Am J Physiol Renal Physiol 2007, 292:F1471-1478
13. Sakurai H: Targeting of TAK1 in inflammatory disorders and cancer, Trends in pharmacological sciences 2012, 33:522-530
14. Rufini A, Tucci P, Celardo I, Melino G: Senescence and aging: the critical roles of p53, Oncogene 2013, 32:5129-5143
15. Tyner S D, Venkatachalam S, Choi J, Jones S, Ghebranious N, Igelmann H, Lu X, Soron G, Cooper B, Brayton C, Park S H, Thompson T, Karsenty G, Bradley A, Donehower L A: p53 mutant mice that display early ageing-associated phenotypes, Nature 2002, 415:45-53
16. Salminen A, Ojala J, Kaarniranta K, Haapasalo A, Hiltunen M, Soininen H: Astrocytes in the aging brain express characteristics of senescence-associated secretory phenotype, Eur J Neurosci 2011, 34:3-11
17. Coppe J P, Patil C K, Rodier F, Krtolica A, Beausejour C M, Parrinello S, Hodgson J G, Chin K, Desprez P Y, Campisi J: A human-like senescence-associated secretory phenotype is conserved in mouse cells dependent on physiological oxygen, PLoS One 2010, 5:e9188

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

We claim:

1. A method for treating a retinal degenerative disease in a subject comprising:
administering to the subject a therapeutically effective amount of anisomycin or functional derivative thereof, wherein the anisomycin or functional derivative thereof reduces cellular senescence in retinal pigment epithelial (RPE) cells, thereby treating the retinal degenerative disease.

2. The method of claim 1, wherein the retinal degenerative disease is selected from the group consisting of dry age-related macular degeneration (AMD), wet AMD, and retinitis pigmentosa.

3. The method of claim 1, wherein the anisomycin or functional derivative thereof is formulated in a pharmaceutical composition that is injected into the ocular space of the subject, formulated as an ocular ointment, or administered by drops to the subject.

4. The method of claim 1, wherein the anisomycin or functional derivative thereof is provided by an implant that is implanted within at least one eye of the subject.

5. The method of claim 1, further comprising administering to the subject at least one additional agent for treatment of a retinal degenerative disease.

* * * * *

SEQUENCE LISTING

```
<160> NUMBER OF SEQ ID NOS: 5

<210> SEQ ID NO 1
<211> LENGTH: 579
<212> TYPE: PRT
<213> ORGANISM: Homo sapiens

<400> SEQUENCE: 1

Met Ser Thr Ala Ser Ala Ala Ser Ser Ser Ser Ser Ser Ala Gly
1               5                   10                  15

Glu Met Ile Glu Ala Pro Ser Gln Val Leu Asn Phe Glu Glu Ile Asp
            20                  25                  30

Tyr Lys Glu Ile Glu Val Glu Glu Val Val Gly Arg Gly Ala Phe Gly
        35                  40                  45

Val Val Cys Lys Ala Lys Trp Arg Ala Lys Asp Val Ala Ile Lys Gln
    50                  55                  60

Ile Glu Ser Glu Ser Glu Arg Lys Ala Phe Ile Val Glu Leu Arg Gln
65                  70                  75                  80

Leu Ser Arg Val Asn His Pro Asn Ile Val Lys Leu Tyr Gly Ala Cys
                85                  90                  95

Leu Asn Pro Val Cys Leu Val Met Glu Tyr Ala Glu Gly Gly Ser Leu
            100                 105                 110

Tyr Asn Val Leu His Gly Ala Glu Pro Leu Pro Tyr Tyr Thr Ala Ala
        115                 120                 125

His Ala Met Ser Trp Cys Leu Gln Cys Ser Gln Gly Val Ala Tyr Leu
    130                 135                 140
```

-continued

His Ser Met Gln Pro Lys Ala Leu Ile His Arg Asp Leu Lys Pro Pro
145                 150                 155                 160

Asn Leu Leu Val Ala Gly Gly Thr Val Leu Lys Ile Cys Asp Phe
        165                 170                 175

Gly Thr Ala Cys Asp Ile Gln Thr His Met Thr Asn Asn Lys Gly Ser
            180                 185                 190

Ala Ala Trp Met Ala Pro Glu Val Phe Glu Gly Ser Asn Tyr Ser Glu
        195                 200                 205

Lys Cys Asp Val Phe Ser Trp Gly Ile Ile Leu Trp Glu Val Ile Thr
    210                 215                 220

Arg Arg Lys Pro Phe Asp Glu Ile Gly Gly Pro Ala Phe Arg Ile Met
225                 230                 235                 240

Trp Ala Val His Asn Gly Thr Arg Pro Pro Leu Ile Lys Asn Leu Pro
                245                 250                 255

Lys Pro Ile Glu Ser Leu Met Thr Arg Cys Trp Ser Lys Asp Pro Ser
            260                 265                 270

Gln Arg Pro Ser Met Glu Glu Ile Val Lys Ile Met Thr His Leu Met
        275                 280                 285

Arg Tyr Phe Pro Gly Ala Asp Glu Pro Leu Gln Tyr Pro Cys Gln Tyr
290                 295                 300

Ser Asp Glu Gly Gln Ser Asn Ser Ala Thr Ser Thr Gly Ser Phe Met
305                 310                 315                 320

Asp Ile Ala Ser Thr Asn Thr Ser Asn Lys Ser Asp Thr Asn Met Glu
                325                 330                 335

Gln Val Pro Ala Thr Asn Asp Thr Ile Lys Arg Leu Glu Ser Lys Leu
            340                 345                 350

Leu Lys Asn Gln Ala Lys Gln Gln Ser Glu Ser Gly Arg Leu Ser Leu
        355                 360                 365

Gly Ala Ser Arg Gly Ser Ser Val Glu Ser Leu Pro Pro Thr Ser Glu
    370                 375                 380

Gly Lys Arg Met Ser Ala Asp Met Ser Glu Ile Glu Ala Arg Ile Ala
385                 390                 395                 400

Ala Thr Thr Gly Asn Gly Gln Pro Arg Arg Arg Ser Ile Gln Asp Leu
                405                 410                 415

Thr Val Thr Gly Thr Glu Pro Gly Gln Val Ser Ser Arg Ser Ser Ser
            420                 425                 430

Pro Ser Val Arg Met Ile Thr Thr Ser Gly Pro Thr Ser Glu Lys Pro
        435                 440                 445

Thr Arg Ser His Pro Trp Thr Pro Asp Asp Ser Thr Asp Thr Asn Gly
    450                 455                 460

Ser Asp Asn Ser Ile Pro Met Ala Tyr Leu Thr Leu Asp His Gln Leu
465                 470                 475                 480

Gln Pro Leu Ala Pro Cys Pro Asn Ser Lys Glu Ser Met Ala Val Phe
                485                 490                 495

Glu Gln His Cys Lys Met Ala Gln Glu Tyr Met Lys Val Gln Thr Glu
            500                 505                 510

Ile Ala Leu Leu Leu Gln Arg Lys Gln Glu Leu Val Ala Glu Leu Asp
        515                 520                 525

Gln Asp Glu Lys Asp Gln Asn Thr Ser Arg Leu Val Gln Glu His
    530                 535                 540

Lys Lys Leu Leu Asp Glu Asn Lys Ser Leu Ser Thr Tyr Tyr Gln Gln
545                 550                 555                 560

Cys Lys Lys Gln Leu Glu Val Ile Arg Ser Gln Gln Gln Lys Arg Gln 565                 570                 575

Gly Thr Ser

<210> SEQ ID NO 2
<211> LENGTH: 606
<212> TYPE: PRT
<213> ORGANISM: Homo sapiens

<400> SEQUENCE: 2

Met Ser Thr Ala Ser Ala Ala Ser Ser Ser Ser Ser Ser Ala Gly
1               5                   10                  15

Glu Met Ile Glu Ala Pro Ser Gln Val Leu Asn Phe Glu Glu Ile Asp
            20                  25                  30

Tyr Lys Glu Ile Glu Val Glu Glu Val Val Gly Arg Gly Ala Phe Gly
            35                  40                  45

Val Val Cys Lys Ala Lys Trp Arg Ala Lys Asp Val Ala Ile Lys Gln
        50                  55                  60

Ile Glu Ser Glu Ser Glu Arg Lys Ala Phe Ile Val Glu Leu Arg Gln
65                  70                  75                  80

Leu Ser Arg Val Asn His Pro Asn Ile Val Lys Leu Tyr Gly Ala Cys
                85                  90                  95

Leu Asn Pro Val Cys Leu Val Met Glu Tyr Ala Glu Gly Gly Ser Leu
            100                 105                 110

Tyr Asn Val Leu His Gly Ala Glu Pro Leu Pro Tyr Tyr Thr Ala Ala
            115                 120                 125

His Ala Met Ser Trp Cys Leu Gln Cys Ser Gln Gly Val Ala Tyr Leu
        130                 135                 140

His Ser Met Gln Pro Lys Ala Leu Ile His Arg Asp Leu Lys Pro Pro
145                 150                 155                 160

Asn Leu Leu Leu Val Ala Gly Gly Thr Val Leu Lys Ile Cys Asp Phe
                165                 170                 175

Gly Thr Ala Cys Asp Ile Gln Thr His Met Thr Asn Asn Lys Gly Ser
            180                 185                 190

Ala Ala Trp Met Ala Pro Glu Val Phe Glu Gly Ser Asn Tyr Ser Glu
        195                 200                 205

Lys Cys Asp Val Phe Ser Trp Gly Ile Ile Leu Trp Glu Val Ile Thr
    210                 215                 220

Arg Arg Lys Pro Phe Asp Glu Ile Gly Gly Pro Ala Phe Arg Ile Met
225                 230                 235                 240

Trp Ala Val His Asn Gly Thr Arg Pro Pro Leu Ile Lys Asn Leu Pro
                245                 250                 255

Lys Pro Ile Glu Ser Leu Met Thr Arg Cys Trp Ser Lys Asp Pro Ser
            260                 265                 270

Gln Arg Pro Ser Met Glu Glu Ile Val Lys Ile Met Thr His Leu Met
        275                 280                 285

Arg Tyr Phe Pro Gly Ala Asp Glu Pro Leu Gln Tyr Pro Cys Gln Tyr
    290                 295                 300

Ser Asp Glu Gly Gln Ser Asn Ser Ala Thr Ser Thr Gly Ser Phe Met
305                 310                 315                 320

Asp Ile Ala Ser Thr Asn Thr Ser Asn Lys Ser Asp Thr Asn Met Glu
                325                 330                 335

Gln Val Pro Ala Thr Asn Asp Thr Ile Lys Arg Leu Glu Ser Lys Leu
            340                 345                 350

Leu Lys Asn Gln Ala Lys Gln Gln Ser Glu Ser Gly Arg Leu Ser Leu

-continued

```
                355                 360                 365
Gly Ala Ser Arg Gly Ser Ser Val Glu Ser Leu Pro Pro Thr Ser Glu
            370                 375                 380
Gly Lys Arg Met Ser Ala Asp Met Ser Glu Ile Glu Ala Arg Ile Ala
385                 390                 395                 400
Ala Thr Thr Ala Tyr Ser Lys Pro Lys Arg Gly His Arg Lys Thr Ala
            405                 410                 415
Ser Phe Gly Asn Ile Leu Asp Val Pro Glu Ile Val Ile Ser Gly Asn
            420                 425                 430
Gly Gln Pro Arg Arg Ser Ile Gln Asp Leu Thr Val Thr Gly Thr
            435                 440                 445
Glu Pro Gly Gln Val Ser Ser Arg Ser Ser Pro Ser Val Arg Met
            450                 455                 460
Ile Thr Thr Ser Gly Pro Thr Ser Glu Lys Pro Thr Arg Ser His Pro
465                 470                 475                 480
Trp Thr Pro Asp Asp Ser Thr Asp Thr Asn Gly Ser Asp Asn Ser Ile
            485                 490                 495
Pro Met Ala Tyr Leu Thr Leu Asp His Gln Leu Gln Pro Leu Ala Pro
            500                 505                 510
Cys Pro Asn Ser Lys Glu Ser Met Ala Val Phe Glu Gln His Cys Lys
            515                 520                 525
Met Ala Gln Glu Tyr Met Lys Val Gln Thr Glu Ile Ala Leu Leu Leu
            530                 535                 540
Gln Arg Lys Gln Glu Leu Val Ala Glu Leu Asp Gln Asp Glu Lys Asp
545                 550                 555                 560
Gln Gln Asn Thr Ser Arg Leu Val Gln Glu His Lys Lys Leu Leu Asp
            565                 570                 575
Glu Asn Lys Ser Leu Ser Thr Tyr Tyr Gln Gln Cys Lys Lys Gln Leu
            580                 585                 590
Glu Val Ile Arg Ser Gln Gln Gln Lys Arg Gln Gly Thr Ser
            595                 600                 605

<210> SEQ ID NO 3
<211> LENGTH: 518
<212> TYPE: PRT
<213> ORGANISM: Homo sapiens

<400> SEQUENCE: 3

Met Ser Thr Ala Ser Ala Ala Ser Ser Ser Ser Ser Ser Ser Ala Gly
1               5                   10                  15
Glu Met Ile Glu Ala Pro Ser Gln Val Leu Asn Phe Glu Glu Ile Asp
            20                  25                  30
Tyr Lys Glu Ile Glu Val Glu Glu Val Val Gly Arg Gly Ala Phe Gly
            35                  40                  45
Val Val Cys Lys Ala Lys Trp Arg Ala Lys Asp Val Ala Ile Lys Gln
        50                  55                  60
Ile Glu Ser Glu Ser Glu Arg Lys Ala Phe Ile Val Glu Leu Arg Gln
65                  70                  75                  80
Leu Ser Arg Val Asn His Pro Asn Ile Val Lys Leu Tyr Gly Ala Cys
            85                  90                  95
Leu Asn Pro Val Cys Leu Val Met Glu Tyr Ala Glu Gly Gly Ser Leu
            100                 105                 110
Tyr Asn Val Leu His Gly Ala Glu Pro Leu Pro Tyr Tyr Thr Ala Ala
            115                 120                 125
```

His Ala Met Ser Trp Cys Leu Gln Cys Ser Gln Gly Val Ala Tyr Leu
130                 135                 140

His Ser Met Gln Pro Lys Ala Leu Ile His Arg Asp Leu Lys Pro Pro
145                 150                 155                 160

Asn Leu Leu Val Ala Gly Gly Thr Val Leu Lys Ile Cys Asp Phe
    165                 170                 175

Gly Thr Ala Cys Asp Ile Gln Thr His Met Thr Asn Asn Lys Gly Ser
            180                 185                 190

Ala Ala Trp Met Ala Pro Glu Val Phe Glu Gly Ser Asn Tyr Ser Glu
        195                 200                 205

Lys Cys Asp Val Phe Ser Trp Gly Ile Ile Leu Trp Glu Val Ile Thr
210                 215                 220

Arg Arg Lys Pro Phe Asp Glu Ile Gly Gly Pro Ala Phe Arg Ile Met
225                 230                 235                 240

Trp Ala Val His Asn Gly Thr Arg Pro Pro Leu Ile Lys Asn Leu Pro
                245                 250                 255

Lys Pro Ile Glu Ser Leu Met Thr Arg Cys Trp Ser Lys Asp Pro Ser
                260                 265                 270

Gln Arg Pro Ser Met Glu Glu Ile Val Lys Ile Met Thr His Leu Met
            275                 280                 285

Arg Tyr Phe Pro Gly Ala Asp Glu Pro Leu Gln Tyr Pro Cys Gln Tyr
290                 295                 300

Ser Asp Glu Gly Gln Ser Asn Ser Ala Thr Ser Thr Gly Ser Phe Met
305                 310                 315                 320

Asp Ile Ala Ser Thr Asn Thr Ser Asn Lys Ser Asp Thr Asn Met Glu
                325                 330                 335

Gln Val Pro Ala Thr Asn Asp Thr Ile Lys Arg Leu Glu Ser Lys Leu
            340                 345                 350

Leu Lys Asn Gln Ala Lys Gln Gln Ser Glu Ser Gly Arg Leu Ser Leu
        355                 360                 365

Gly Ala Ser Arg Gly Ser Ser Val Glu Ser Leu Pro Pro Thr Ser Glu
370                 375                 380

Gly Lys Arg Met Ser Ala Asp Met Ser Glu Ile Glu Ala Arg Ile Ala
385                 390                 395                 400

Ala Thr Thr Ala Tyr Ser Lys Pro Lys Arg Gly His Arg Lys Thr Ala
                405                 410                 415

Ser Phe Gly Asn Ile Leu Asp Val Pro Glu Ile Val Ile Ser Gly Asn
            420                 425                 430

Gly Gln Pro Arg Arg Ser Ile Gln Asp Leu Thr Val Thr Gly Thr
        435                 440                 445

Glu Pro Gly Gln Val Ser Ser Arg Ser Ser Ser Pro Ser Val Arg Met
450                 455                 460

Ile Thr Thr Ser Gly Pro Thr Ser Glu Lys Pro Thr Arg Ser His Pro
465                 470                 475                 480

Trp Thr Pro Asp Asp Ser Thr Asp Thr Asn Gly Ser Asp Asn Ser Ile
                485                 490                 495

Pro Met Ala Tyr Leu Thr Leu Asp His Gln Leu Gln Ala Arg Thr Ser
            500                 505                 510

Cys Arg Thr Gly Pro Gly
        515

<210> SEQ ID NO 4
<211> LENGTH: 491
<212> TYPE: PRT

<213> ORGANISM: Homo sapiens

<400> SEQUENCE: 4

| Met | Ser | Thr | Ala | Ser | Ala | Ala | Ser | Ser | Ser | Ser | Ser | Ser | Ala | Gly |
|---|---|---|---|---|---|---|---|---|---|---|---|---|---|---|
| 1 | | | | 5 | | | | | 10 | | | | | 15 |

Glu Met Ile Glu Ala Pro Ser Gln Val Leu Asn Phe Glu Glu Ile Asp
        20                  25                  30

Tyr Lys Glu Ile Glu Val Glu Glu Val Val Gly Arg Gly Ala Phe Gly
            35                  40                  45

Val Val Cys Lys Ala Lys Trp Arg Ala Lys Asp Val Ala Ile Lys Gln
 50                  55                  60

Ile Glu Ser Glu Ser Glu Arg Lys Ala Phe Ile Val Glu Leu Arg Gln
 65                  70                  75                  80

Leu Ser Arg Val Asn His Pro Asn Ile Val Lys Leu Tyr Gly Ala Cys
                85                  90                  95

Leu Asn Pro Val Cys Leu Val Met Glu Tyr Ala Glu Gly Gly Ser Leu
            100                 105                 110

Tyr Asn Val Leu His Gly Ala Glu Pro Leu Pro Tyr Tyr Thr Ala Ala
            115                 120                 125

His Ala Met Ser Trp Cys Leu Gln Cys Ser Gln Gly Val Ala Tyr Leu
 130                 135                 140

His Ser Met Gln Pro Lys Ala Leu Ile His Arg Asp Leu Lys Pro Pro
145                 150                 155                 160

Asn Leu Leu Leu Val Ala Gly Gly Thr Val Leu Lys Ile Cys Asp Phe
                165                 170                 175

Gly Thr Ala Cys Asp Ile Gln Thr His Met Thr Asn Asn Lys Gly Ser
            180                 185                 190

Ala Ala Trp Met Ala Pro Glu Val Phe Glu Gly Ser Asn Tyr Ser Glu
            195                 200                 205

Lys Cys Asp Val Phe Ser Trp Gly Ile Ile Leu Trp Glu Val Ile Thr
 210                 215                 220

Arg Arg Lys Pro Phe Asp Glu Ile Gly Gly Pro Ala Phe Arg Ile Met
225                 230                 235                 240

Trp Ala Val His Asn Gly Thr Arg Pro Pro Leu Ile Lys Asn Leu Pro
                245                 250                 255

Lys Pro Ile Glu Ser Leu Met Thr Arg Cys Trp Ser Lys Asp Pro Ser
            260                 265                 270

Gln Arg Pro Ser Met Glu Glu Ile Val Lys Ile Met Thr His Leu Met
            275                 280                 285

Arg Tyr Phe Pro Gly Ala Asp Glu Pro Leu Gln Tyr Pro Cys Gln Tyr
 290                 295                 300

Ser Asp Glu Gly Gln Ser Asn Ser Ala Thr Ser Thr Gly Ser Phe Met
305                 310                 315                 320

Asp Ile Ala Ser Thr Asn Thr Ser Asn Lys Ser Asp Thr Asn Met Glu
                325                 330                 335

Gln Val Pro Ala Thr Asn Asp Thr Ile Lys Arg Leu Glu Ser Lys Leu
            340                 345                 350

Leu Lys Asn Gln Ala Lys Gln Gln Ser Glu Ser Gly Arg Leu Ser Leu
            355                 360                 365

Gly Ala Ser Arg Gly Ser Ser Val Glu Ser Leu Pro Pro Thr Ser Glu
 370                 375                 380

Gly Lys Arg Met Ser Ala Asp Met Ser Glu Ile Glu Ala Arg Ile Ala
385                 390                 395                 400

-continued

Ala Thr Thr Gly Asn Gly Gln Pro Arg Arg Ser Ile Gln Asp Leu
                    405                 410                 415

Thr Val Thr Gly Thr Glu Pro Gly Gln Val Ser Ser Arg Ser Ser Ser
            420                 425                 430

Pro Ser Val Arg Met Ile Thr Thr Ser Gly Pro Thr Ser Glu Lys Pro
            435                 440                 445

Thr Arg Ser His Pro Trp Thr Pro Asp Asp Ser Thr Asp Thr Asn Gly
    450                 455                 460

Ser Asp Asn Ser Ile Pro Met Ala Tyr Leu Thr Leu Asp His Gln Leu
465                 470                 475                 480

Gln Ala Arg Thr Ser Cys Arg Thr Gly Pro Gly
            485                 490

<210> SEQ ID NO 5
<211> LENGTH: 504
<212> TYPE: PRT
<213> ORGANISM: Homo sapiens

<400> SEQUENCE: 5

Met Ala Ala Gln Arg Arg Ser Leu Leu Gln Ser Glu Gln Gln Pro Ser
1               5                   10                  15

Trp Thr Asp Asp Leu Pro Leu Cys His Leu Ser Gly Val Gly Ser Ala
                20                  25                  30

Ser Asn Arg Ser Tyr Ser Ala Asp Gly Lys Gly Thr Glu Ser His Pro
            35                  40                  45

Pro Glu Asp Ser Trp Leu Lys Phe Arg Ser Glu Asn Asn Cys Phe Leu
        50                  55                  60

Tyr Gly Val Phe Asn Gly Tyr Asp Gly Asn Arg Val Thr Asn Phe Val
65                  70                  75                  80

Ala Gln Arg Leu Ser Ala Glu Leu Leu Leu Gly Gln Leu Asn Ala Glu
                85                  90                  95

His Ala Glu Ala Asp Val Arg Arg Val Leu Leu Gln Ala Phe Asp Val
            100                 105                 110

Val Glu Arg Ser Phe Leu Glu Ser Ile Asp Asp Ala Leu Ala Glu Lys
        115                 120                 125

Ala Ser Leu Gln Ser Gln Leu Pro Glu Gly Val Pro Gln His Gln Leu
130                 135                 140

Pro Pro Gln Tyr Gln Lys Ile Leu Glu Arg Leu Lys Thr Leu Glu Arg
145                 150                 155                 160

Glu Ile Ser Gly Gly Ala Met Ala Val Val Ala Val Leu Leu Asn Asn
                165                 170                 175

Lys Leu Tyr Val Ala Asn Val Gly Thr Asn Arg Ala Leu Leu Cys Lys
            180                 185                 190

Ser Thr Val Asp Gly Leu Gln Val Thr Gln Leu Asn Val Asp His Thr
        195                 200                 205

Thr Glu Asn Glu Asp Glu Leu Phe Arg Leu Ser Gln Leu Gly Leu Asp
    210                 215                 220

Ala Gly Lys Ile Lys Gln Val Gly Ile Ile Cys Gly Gln Glu Ser Thr
225                 230                 235                 240

Arg Arg Ile Gly Asp Tyr Lys Val Lys Tyr Gly Tyr Thr Asp Ile Asp
                245                 250                 255

Leu Leu Ser Ala Ala Lys Ser Lys Pro Ile Ile Ala Glu Pro Glu Ile
            260                 265                 270

His Gly Ala Gln Pro Leu Asp Gly Val Thr Gly Phe Leu Val Leu Met
        275                 280                 285

-continued

```
Ser Glu Gly Leu Tyr Lys Ala Leu Glu Ala Ala His Gly Pro Gly Gln
    290                 295                 300

Ala Asn Gln Glu Ile Ala Ala Met Ile Asp Thr Glu Phe Ala Lys Gln
305                 310                 315                 320

Thr Ser Leu Asp Ala Val Ala Gln Ala Val Val Asp Arg Val Lys Arg
                325                 330                 335

Ile His Ser Asp Thr Phe Ala Ser Gly Gly Glu Arg Ala Arg Phe Cys
                340                 345                 350

Pro Arg His Glu Asp Met Thr Leu Leu Val Arg Asn Phe Gly Tyr Pro
        355                 360                 365

Leu Gly Glu Met Ser Gln Pro Thr Pro Ser Pro Ala Pro Ala Ala Gly
    370                 375                 380

Gly Arg Val Tyr Pro Val Ser Val Pro Tyr Ser Ser Ala Gln Ser Thr
385                 390                 395                 400

Ser Lys Thr Ser Val Thr Leu Ser Leu Val Met Pro Ser Gln Gly Gln
                405                 410                 415

Met Val Asn Gly Ala His Ser Ala Ser Thr Leu Asp Glu Ala Thr Pro
                420                 425                 430

Thr Leu Thr Asn Gln Ser Pro Thr Leu Thr Leu Gln Ser Thr Asn Thr
            435                 440                 445

His Thr Gln Ser Ser Ser Ser Ser Asp Gly Gly Leu Phe Arg Ser
    450                 455                 460

Arg Pro Ala His Ser Leu Pro Pro Gly Glu Asp Gly Arg Val Glu Pro
465                 470                 475                 480

Tyr Val Asp Phe Ala Glu Phe Tyr Arg Leu Trp Ser Val Asp His Gly
                485                 490                 495

Glu Gln Ser Val Val Thr Ala Pro
                500
```